United States Patent [19]

Sprecker et al.

[11] 4,209,543
[45] Jun. 24, 1980

[54] FLAVORING WITH A MIXTURE OF ACETYL HYDRINDACENES

[75] Inventors: Mark A. Sprecker, Sea Bright; Manfred H. Vock, Locust; Frederick L. Schmitt, Holmdel; Joaquin Vinals, Red Bank, all of N.J.; Jacob Kiwala, Brooklyn, N.Y.

[73] Assignee: International Flavors & Fragrances Inc., New York, N.Y.

[21] Appl. No.: 953,180

[22] Filed: Oct. 20, 1978

[51] Int. Cl.² ............................................. A23L 1/235
[52] U.S. Cl. .................................. 426/538; 568/326; 568/327; 568/319
[58] Field of Search ......................... 260/592; 426/538

[56] References Cited

U.S. PATENT DOCUMENTS

| | | | |
|---|---|---|---|
| 3,078,319 | 2/1963 | Wood | 260/592 UX |
| 3,152,192 | 10/1964 | Wood et al. | 260/592 UX |
| 3,244,751 | 4/1966 | Theimer et al. | 260/592 |
| 3,347,946 | 10/1967 | Wood et al. | 260/592 X |
| 3,400,159 | 9/1968 | Theimer et al. | 260/592 |

OTHER PUBLICATIONS

Arctander, Perfume and Flavor Chemicals, vol. I and II, 1969, Published by the Author: Montclair N.J., Items No. 105, 140, 811, 813, 923, 1326, 2278, 2279, 2414, 2444.
Fenaroli's Handbook of Flavor Ingredients, Edited by Furia et al., 1st Ed., 1971, Chemical Rubber Co., Cleveland, p. 168.

*Primary Examiner*—Joseph M. Golian
*Attorney, Agent, or Firm*—Arthur L. Liberman; Franklin D. Wolffe

[57] ABSTRACT

Processes and compositions are described for the use in foodstuff flavor and aroma, tobacco flavor and aroma and perfume and perfumed article aroma augmenting, modifying, altering and enhancing compositions and as foodstuff, chewing gum, toothpaste, medicinal product, tobacco, perfume and perfumed article aroma imparting materials of acetyl hydrindacenes and acetyl indanes and mixtures of same, said acetyl indanes and acetyl hydrindacenes having the structures:

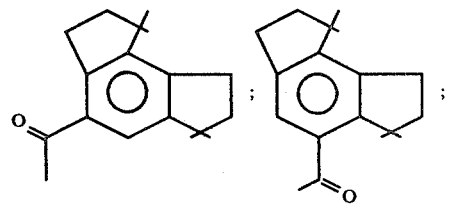

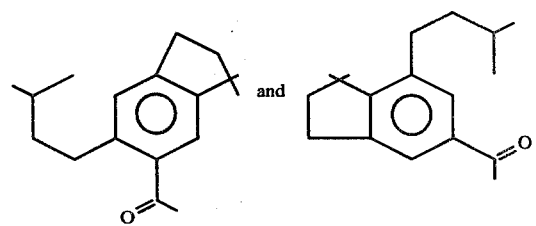

and existing in the liquid phase at ambient temperature and pressure.

Addition of said acetyl hydrindacenes and acetyl indanes and mixtures of same is indicated to produce:
 (a) In food flavorings, a musky aroma and musky and sweet flavor characteristics (useful in pear, peach and apricot flavors);
 (b) In tobacco, a sweet, floral, musk aroma prior to smoking and a sweet, floral, musk aroma augmenting effect in the main stream and in the side stream on smoking; and
 (c) In perfumes and perfumed articles, rich, animal-musk, sweet, floral and sandalwoodlike aromas.

1 Claim, 13 Drawing Figures

GLC PROFILE FOR EXAMPLE II.

GLC PROFILE FOR EXAMPLE I.

GLC PROFILE FOR EXAMPLE III.

NMR SPECTRUM FOR EXAMPLE III.

FIG. 6 GLC PROFILE FOR EXAMPLE IV.

GLC PROFILE FOR EXAMPLE V

FIG. 10 NMR SPECTRUM FOR EXAMPLE V

IR SPECTRUM FOR EXAMPLE V

NMR SPECTRUM FOR EXAMPLE V

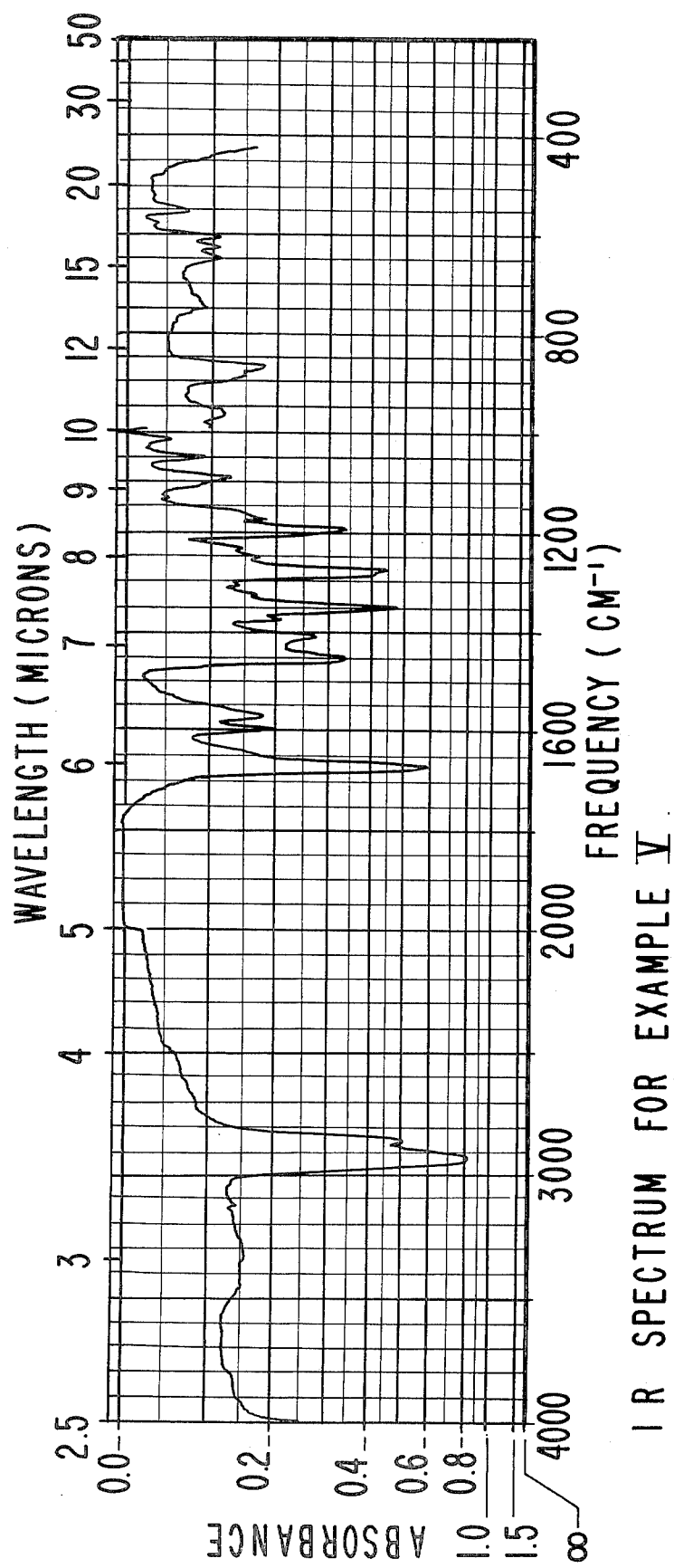
FIG.13 IR SPECTRUM FOR EXAMPLE V

FLAVORING WITH A MIXTURE OF ACETYL HYDRINDACENES

BACKGROUND OF THE INVENTION

The present invention relates to acetyl hydrindacenes and acetyl indanes and mixtures of same as well as organoleptic uses thereof to alter, modify, augment, enhance or impart flavors and/or aromas of (or to) consumable materials.

There has been considerable work performed relating to substances which can be used to impart (or alter, modify or enhance) flavors and fragrances to (or in) various consumable materials. These substances are used to diminish the use of natural materials, some of which may be in short supply and to provide more uniform properties in the finished product. Musky aromas and musky and sweet flavor characteristics are particularly desirable for many uses in foodstuff flavors, particularly apricot, peach and pear flavors. Rich, animal musk, floral and sandalwood-like aromas are desirable in several types of perfume compositions and for use in perfumed articles. Sweet, floral, musk notes are desirable in smoking tobacco flavor compositions and for use in conjunction with smoking tobaccos.

U.S. Pat. No. 3,244,751 issued on Apr. 5, 1966 discloses the reaction of 1,1,6,6-tetramethyl-as-hydrindacene with acetyl chloride to form 4-acetyl-1,1,6,6-tetramethyl-as-hydrindacene, useful for its properties as a perfumery material according to the following reaction:

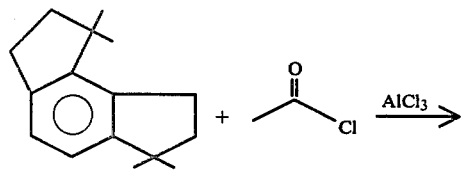

The use of acetyl chloride rather than other acylating agents such as acetic anhydride gives rise to the production of the specific isomer having the structure:

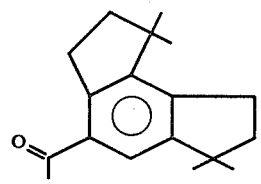

(which exists in the solid phase crystalline form at ambient temperature and pressure and which has sandalwood aroma notes), rather than the mixture of isomers having the structures:

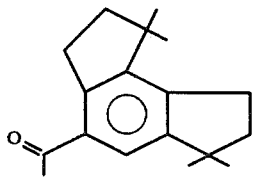

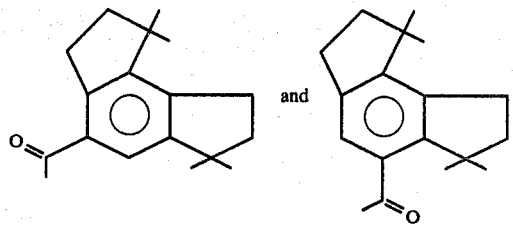

(which exists in the liquid phase at ambient temperature and pressure).

At column 6, lines 5-32 of U.S. Pat. No. 3,347,946, 5-acetyl-3,3,8,8-tetramethyl-as-hydrindacene is indicated to have been prepared from 5-isopropyl-3,3,8,8-tetramethyl-as-hydrindacene by means of the reaction of acetic anhydride with 5-isopropyl-3,3,8,8-tetramethyl-as-hydrindacene in the presence of aluminum chloride and ethylene dichloride. The reaction product was indicated in said U.S. Pat. No. 3,347,946 to have a "persistent musk-like odor" and to be "suitable as a fixative in perfumery". When, however, a reaction procedure is used wherein the aluminum chloride is added to the 5-isopropyl-3,3,8,8-tetramethyl-as-hydrindacene at 0° C., a 60:40 mixture of two isomers is obtained:

60% of the isomer having the structure:

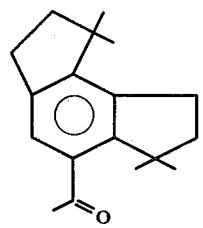

and 40% of the isomer having the structure:

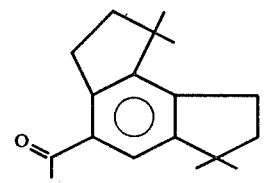

When it is attempted to carry out the same reaction at 20° C. only the compound having the structure:

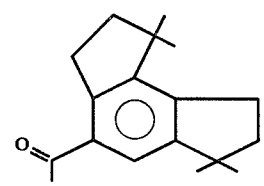

(existing as a solid at ambient temperatures and pressures) is obtained. On the other hand, if a mixture of 5-isopropyl-3,3,8,8-tetramethyl-as-hydrindacene, and acetic anhydride is added to a stirred slurry of aluminum chloride at 0° C., a mixture of four compounds is obtained, to wit:

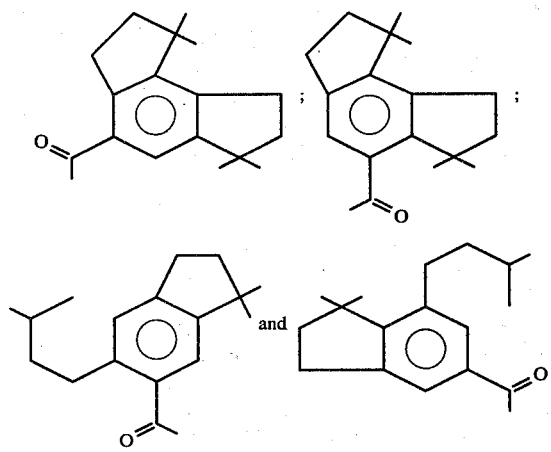

(the mixture existing in the liquid phase at ambient temperature and pressure).

Accordingly, the prior art does not explicitly or implicitly indicate the technique for preparation of mixtures of isomers of acetyl hydrindacenes or acetyl indanes having the structures:

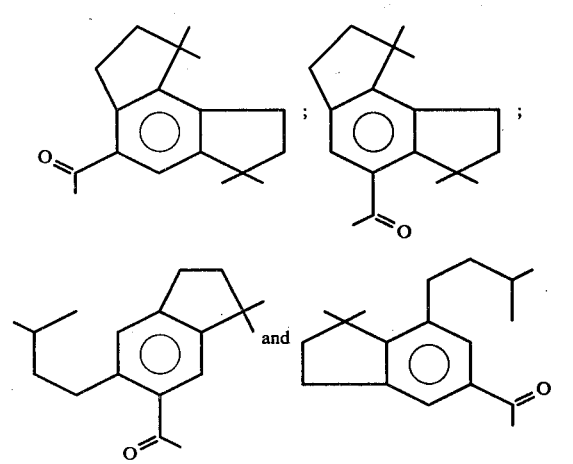

using hydrindacenes having the structure:

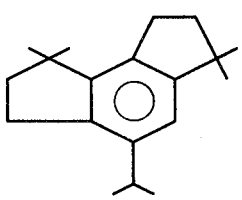

as a starting material; nor does the prior art disclose that acetyl indanes, acetyl hydrindacenes or mixtures of same can be produced as liquids at ambient temperatures and pressures thereby enabling them to be used in a commercially advantageous manner since it is no longer necessary to use additional solvents to cause such materials to be incorporated into standard liquid perfume compositions or colognes or liquid flavor compositions or intimately admixed with either solid or liquid perfumed article compositions, e.g., anionic, cationic or nonionic detergents.

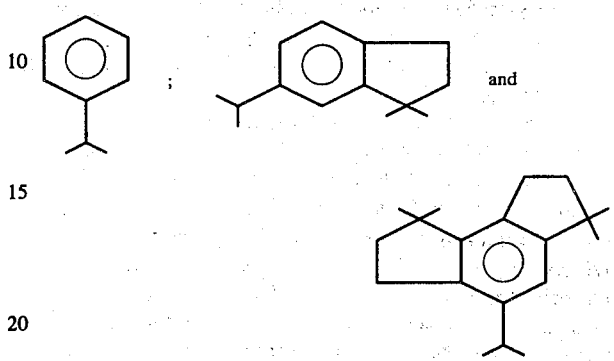

Figure 2:
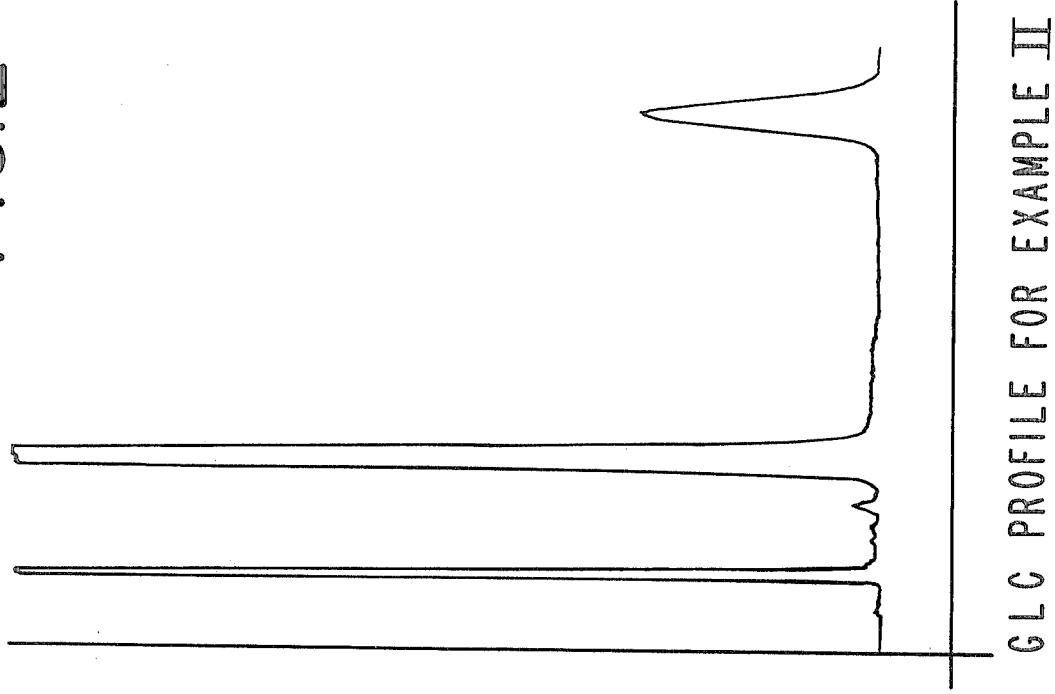

FIG. 2 is the GLC profile for the reaction product of Example II containing compounds having the structures:

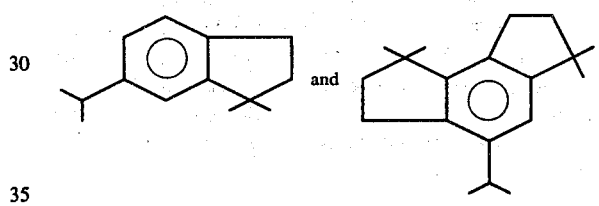

Figure 3:
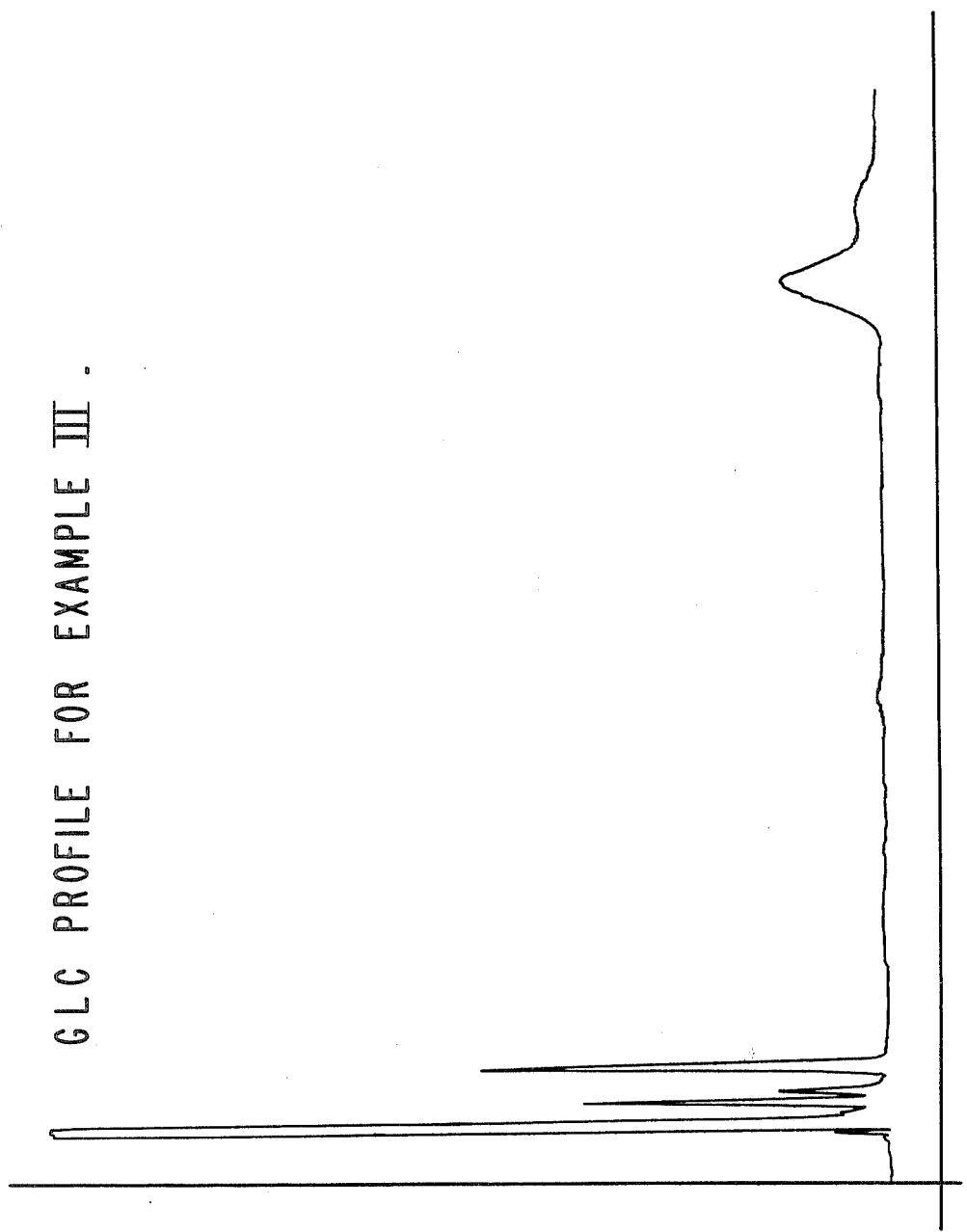

FIG. 3 is the GLC profile for the reaction product of Example III containing the compound having the structure:

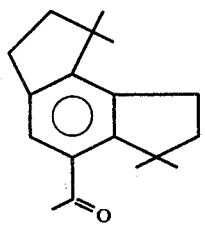

Figure 4:
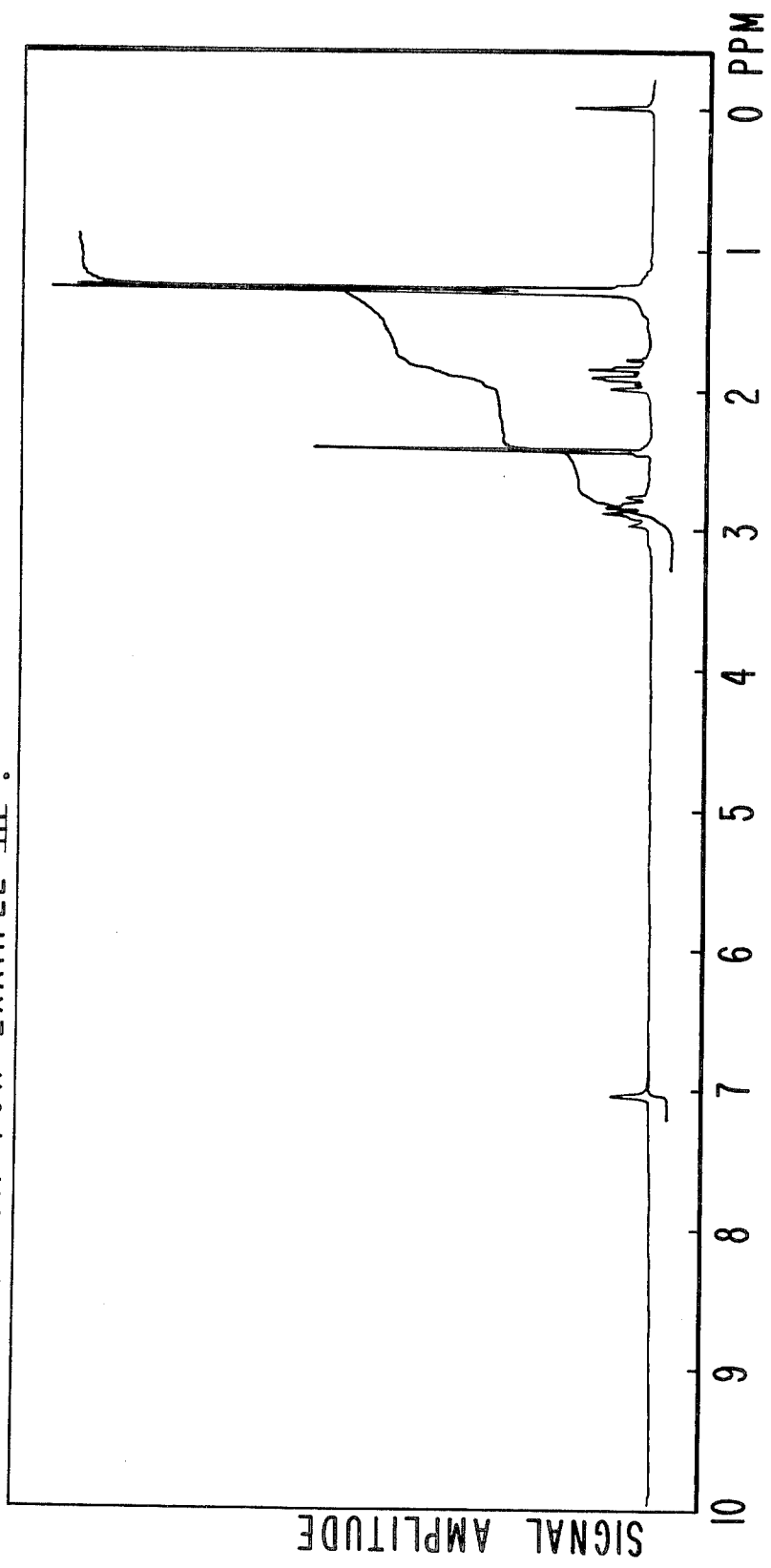

FIG. 4 is the NMR spectrum for the compound having the structure:

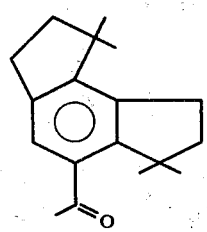

produced according to Example III.

Figure 5:
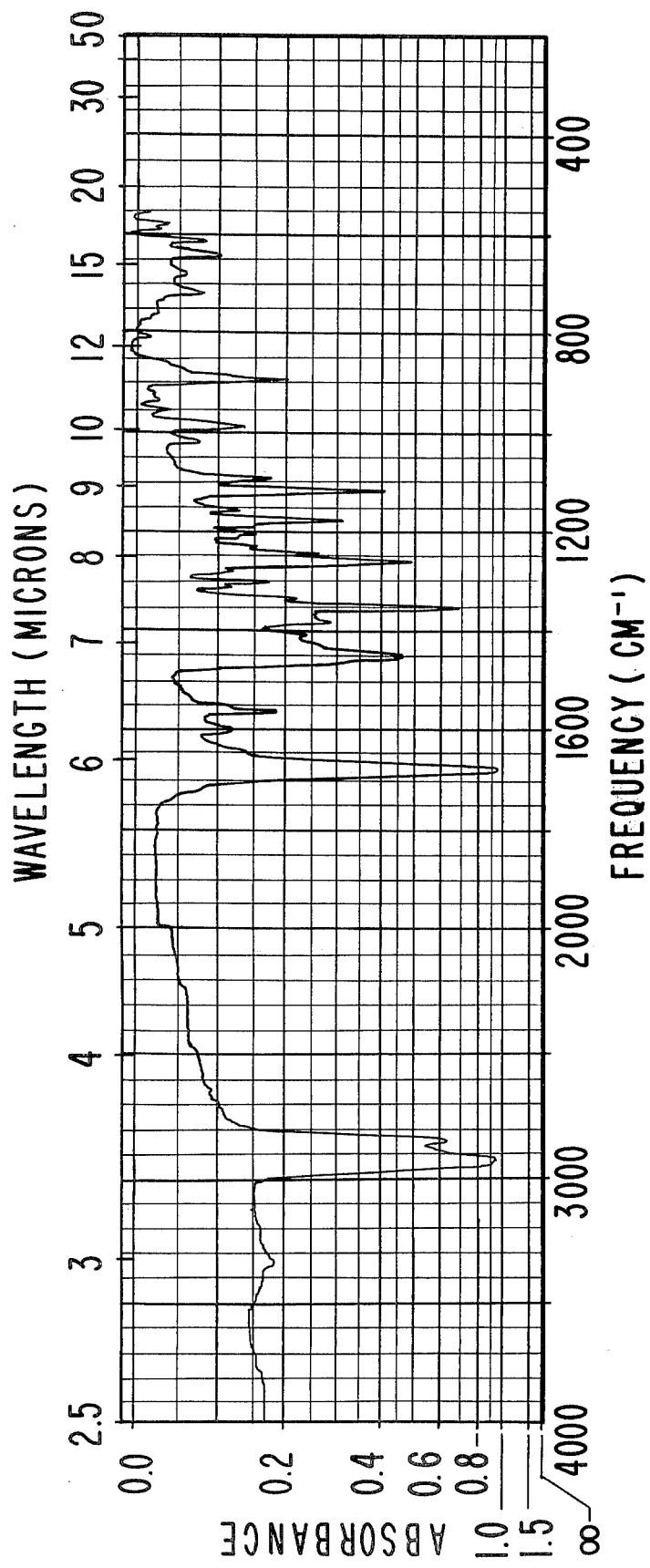

FIG. 5 is the infra-red spectrum for the compound having the structure:

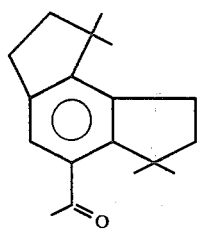

produced according to Example III.

Figure 6:
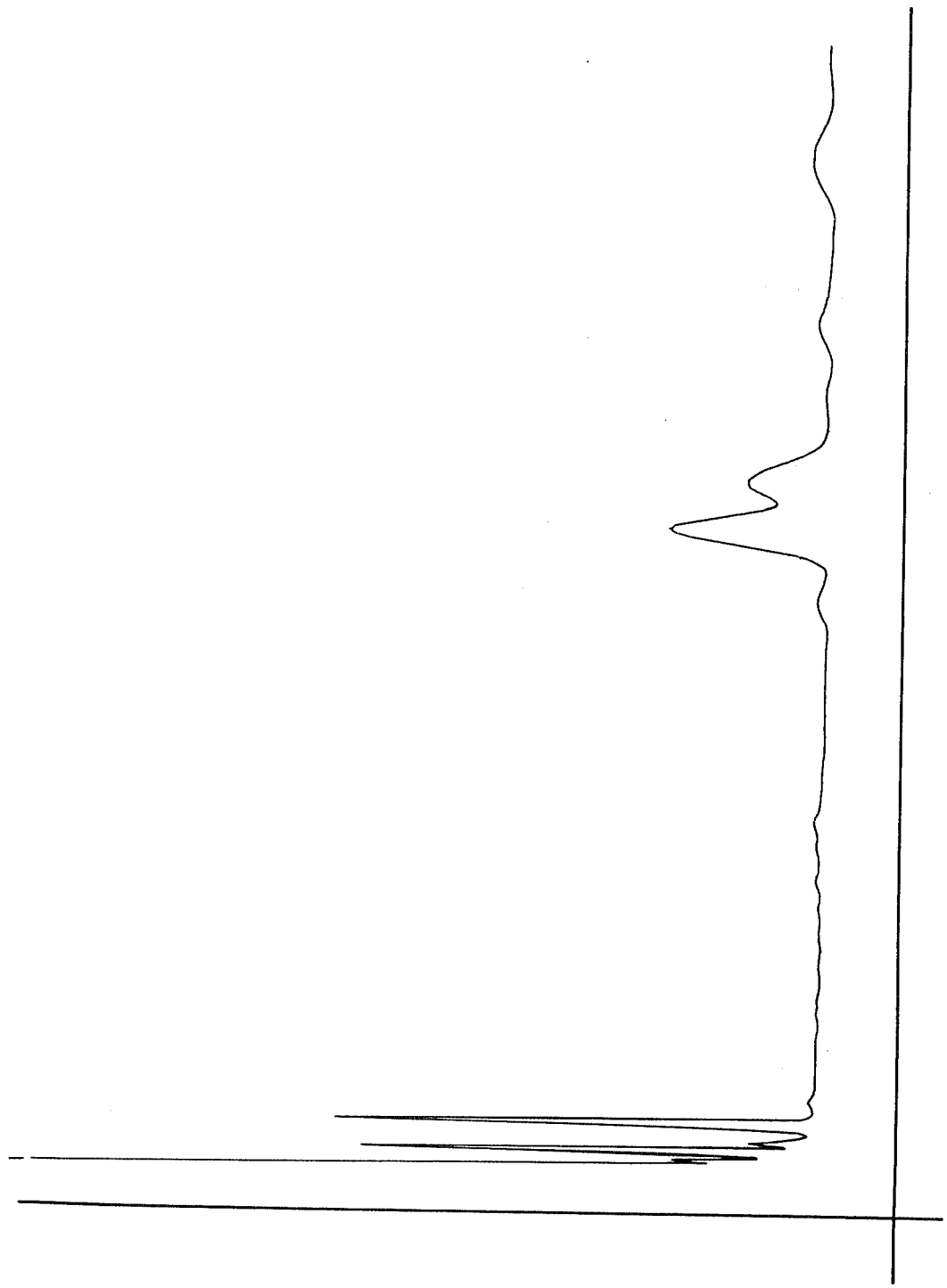

FIG. 6 is the GLC profile for the reaction product produced according to Example IV, containing compounds having the structures:

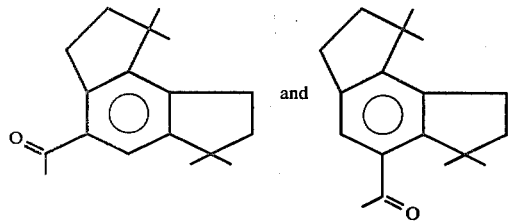

Figure 7:
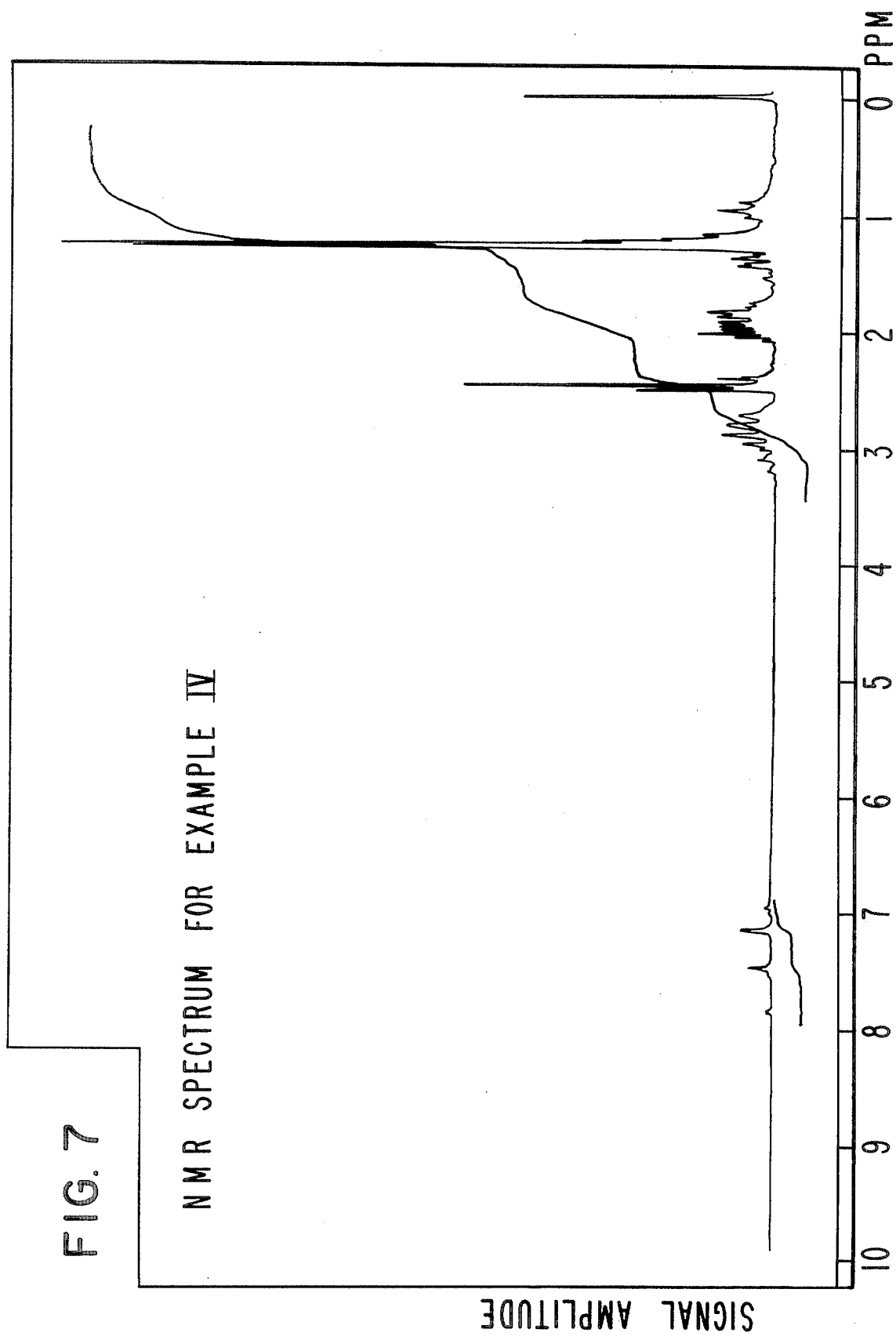

FIG. 7 is the NMR spectrum for the reaction product of Example IV, containing compounds having the structures:

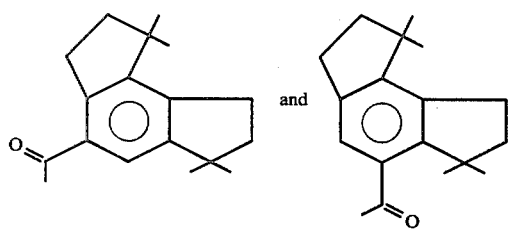

Figure 8:
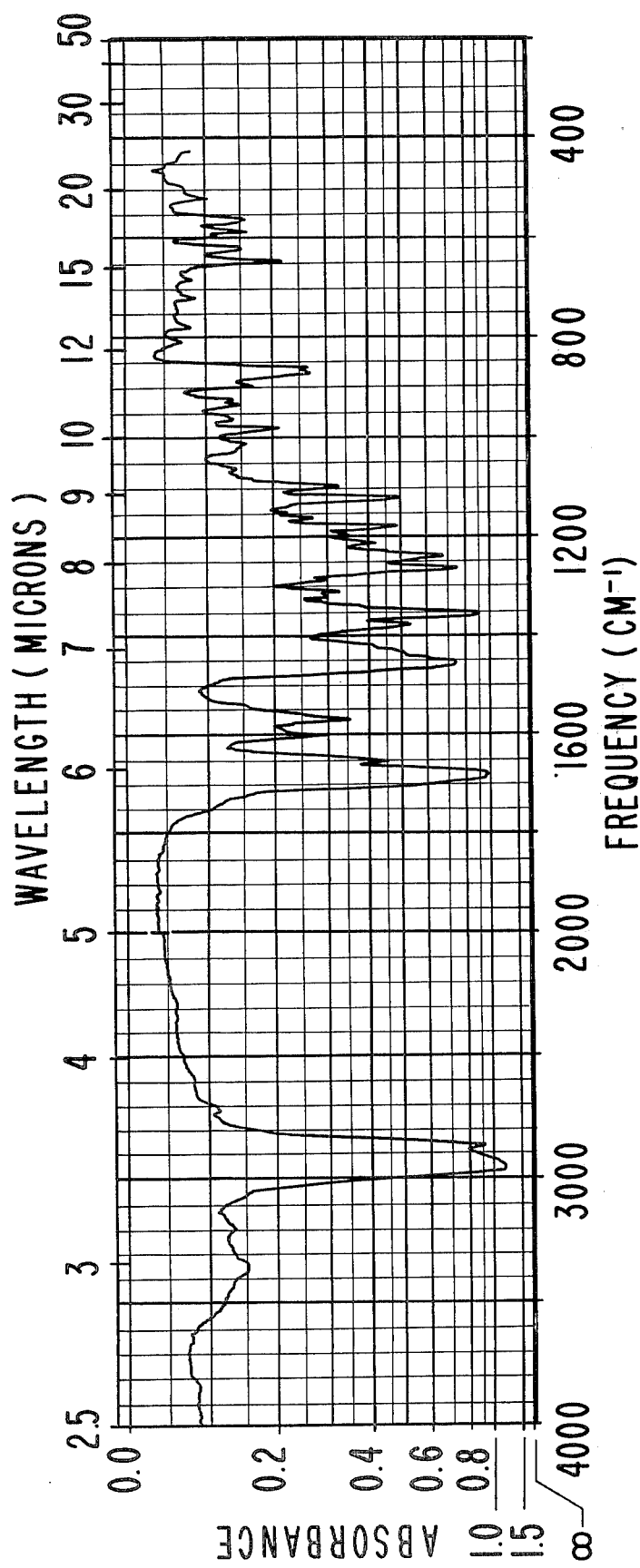

FIG. 8 is the infra-red spectrum for the reaction product of Example IV containing compounds having the structures:

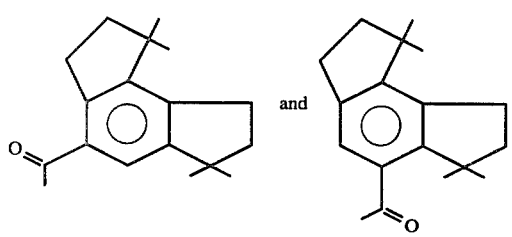

Figure 9:
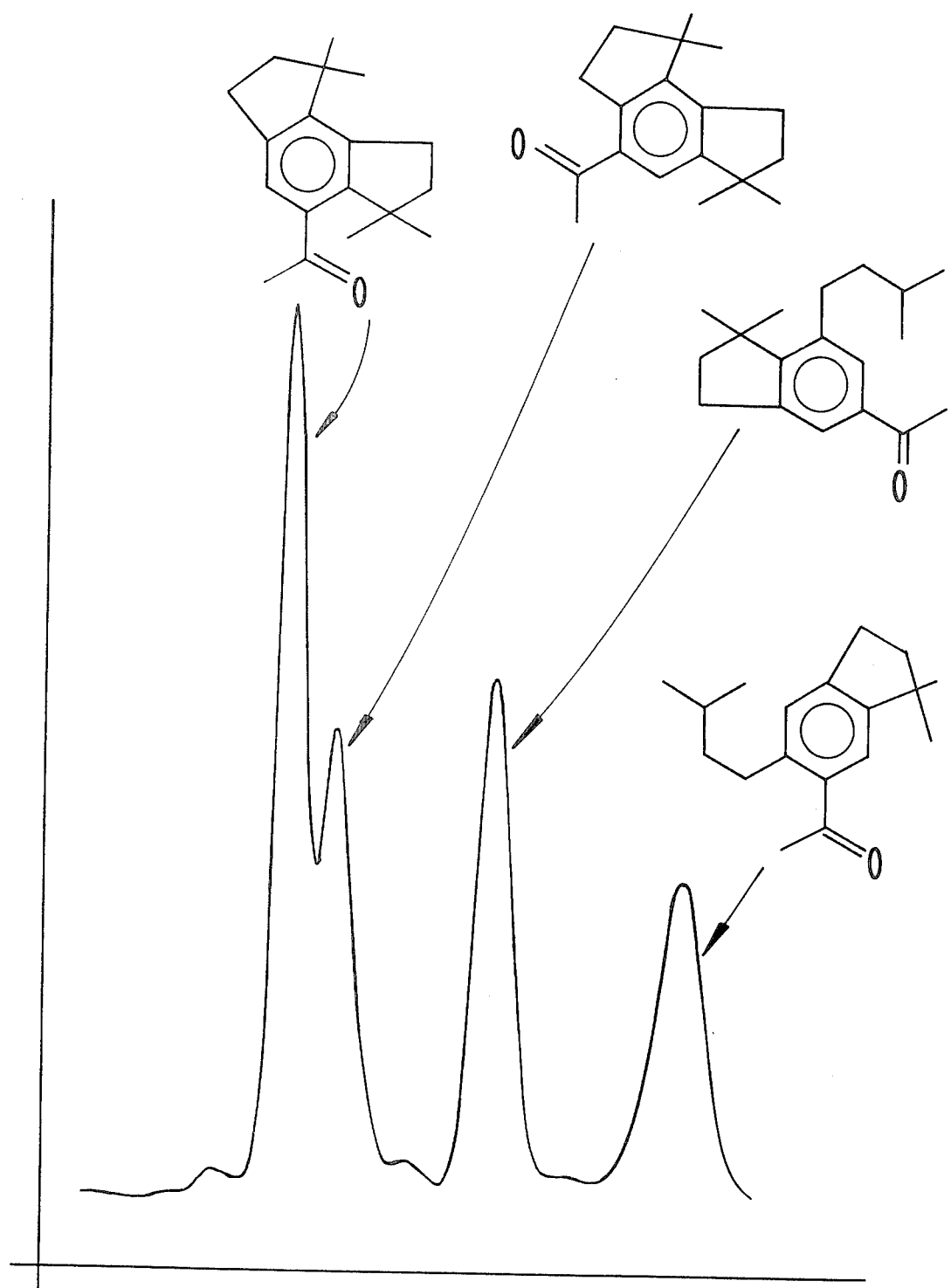

FIG. 9 is the GLC profile for the reaction product of Example V containing the compounds having the structures:

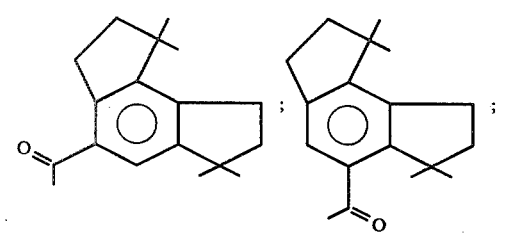

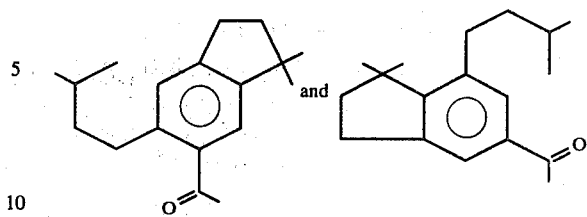

Figure 10:
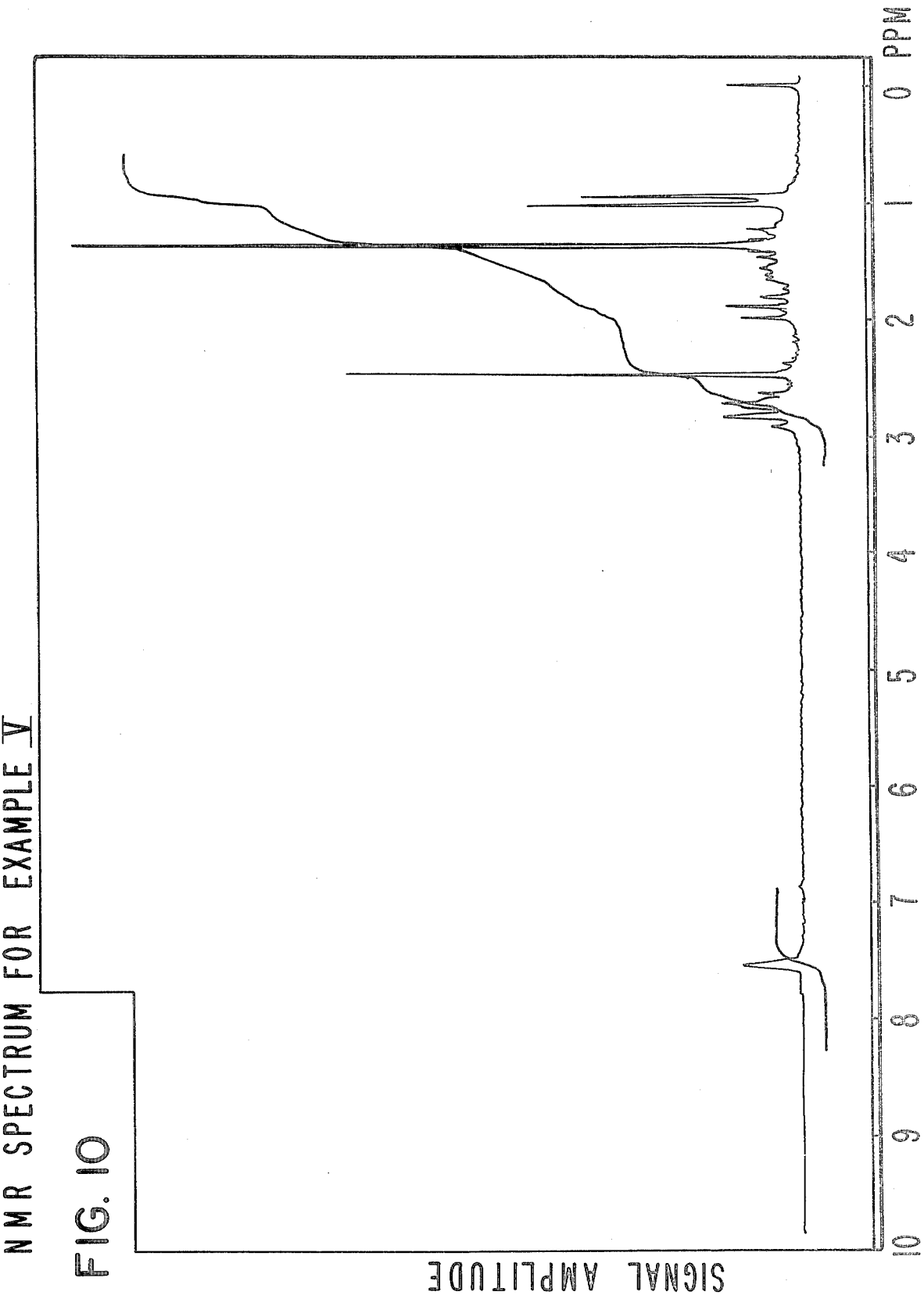

FIG. 10 is the NMR spectrum for the compound having the structure:

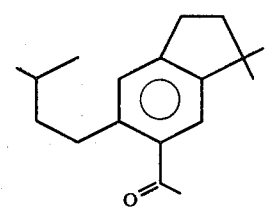

produced according to Example V.

Figure 11:
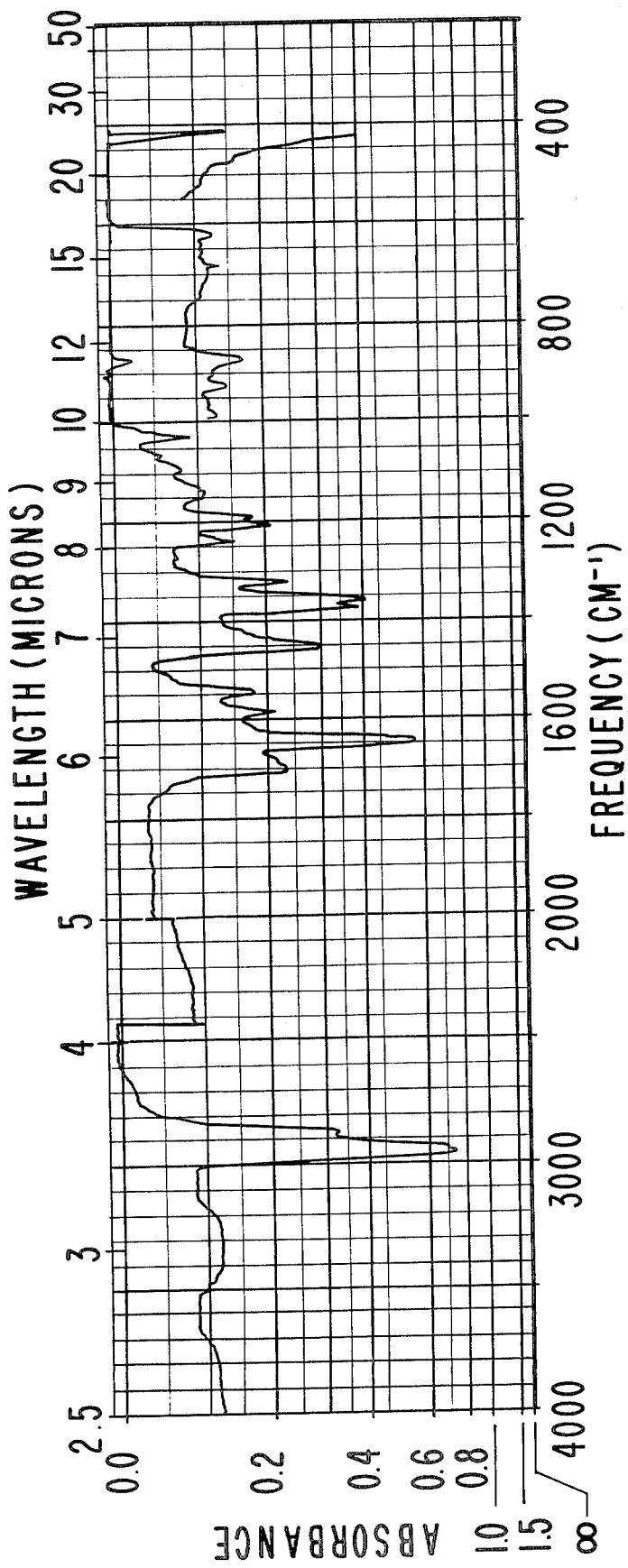

FIG. 11 is the infra-red spectrum for the compound having the structure:

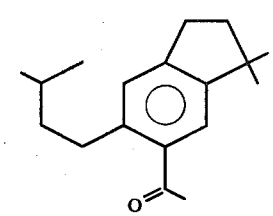

produced according to Example V.

Figure 12:
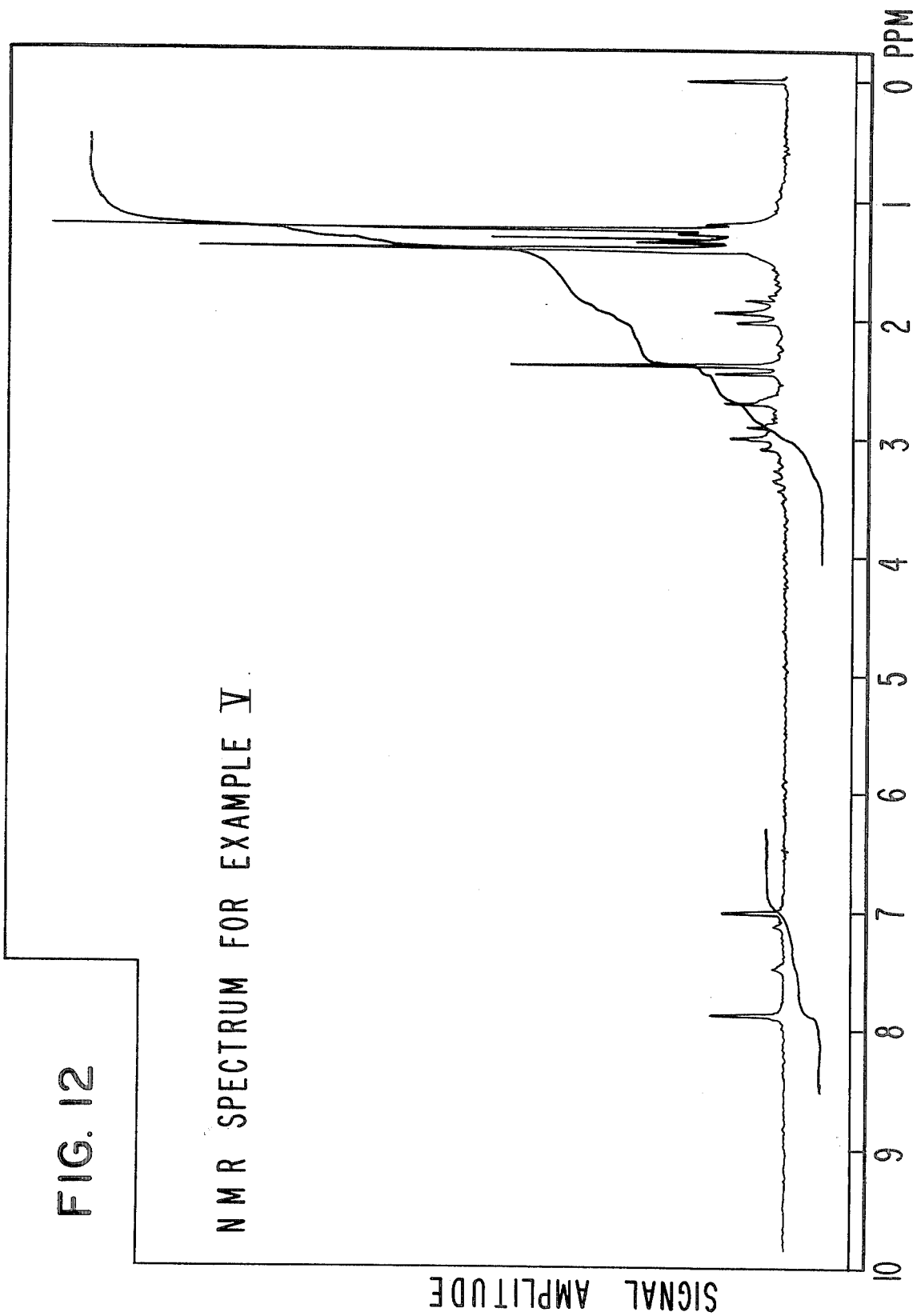

FIG. 12 is the NMR spectrum for the compound having the structure:

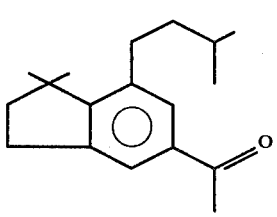

produced according to Example V.

FIG. 13 is the infra-red spectrum for the compound having the structure:

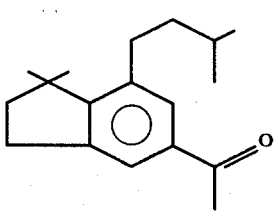

produced according to Example V.

THE INVENTION

It has now been discovered that novel solid and liquid foodstuf, chewing gum, medicinal product, and flavoring compositions having pear, peach or apricot flavor with musky aroma characteristics and musky and sweet flavor characteristics; novel perfume compositions and perfumed articles having rich, animal musk, sweet, floral and surprisingly intense sandalwood aromas; as well as novel smoking tobacco compositions and smoking tobacco flavoring compositions having sweet, floral and musk aromas and tastes on smoking and prior to smoking in the main stream and in the side stream may be provided by the novel acetyl hydrindacene derivatives and novel mixtures of acetyl hydrindacene derivatives and acetyl indane derivatives and novel acetyl indane derivatives of our invention. The novel acetyl hydrindacene of our invention has the structure:

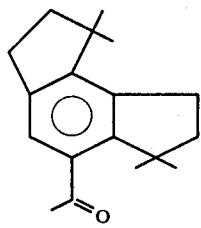

The novel acetyl indane compounds of our invention have the structures:

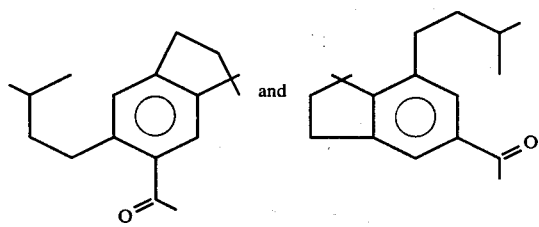

The novel mixtures of our invention contain compounds having the structures:

(I):

(II):

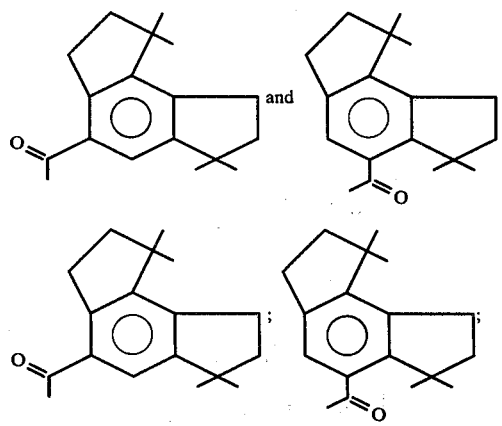

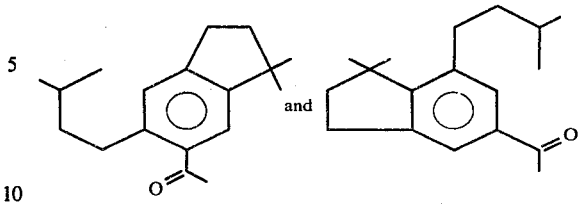

In addition to having the abilities to impart (augment or enhance) (in a novel manner) organoleptic properties to (or in) consumable materials as set forth supra, the acetyl hydrindacenes, acetyl indanes, mixtures of acetyl hydrindacenes and mixtures of acetyl hydrindacenes and acetyl indanes of our invention surprisingly exist in the liquid phase at ambient temperatures and pressure (e.g., 10° C.–35° C. at one atmosphere pressure) which physical properties enable them to be used in flavor and fragrance compositions and perfumed articles in the absence of any additional liquid carriers or solvents which, in many instances, must be totally removed from said flavor and fragrance compositions or perfumed articles prior to entry thereof into the main stream of commerce.

The novel acetyl hydrindacenes, acetyl indanes, and mixtures of actyl hydrindacenes and mixtures of acetyl hydrindacenes and acetyl indanes of our invention are prepared from 5-isopropyl-3,3,8,8-tetramethyl-as-hydrindacene. The 4-isopropyl-3,3,8,8-tetramethyl-as-hydrindacene can be prepared by the reaction at from about 0° C. up to about 5° C. of isoprene and cumene in the presence of sulfuric acid to form a mixture of 6-isopropyl-1,1-dimethylindane and the aforementioned 4-isopropyl-3,3,8,8-tetramethyl-as-hydrindacenes (as set forth in reaction scheme III, infra). Alternatively, cumene, isoprene and 6-isopropyl-1,1-dimethylindane can be reacted in the presence of sulfuric acid to form 4-isopropyl-3,3,8,8-tetramethyl-as-hydrindacene along with recovered cumene and 6-isopropyl-1,1-dimethylindane. In the latter scheme (scheme IV as set forth infra) the mole ratio of cumene to 6-isopropyl-1,1-dimethylindane may be adjusted such that the net amount of 6-isopropyl-1,1-dimethylindane formed during the reaction is equal to the amount originally charged into the reaction mass.

Thus, the mole ratio of the 6-isopropyl-1,1-dimethylindane:cumene may be within the range of from about 2:1 up to about 3:1. The mole ratio of the sum of cumene and 6-isopropyl-1,1-dimethylindane:isoprene may be within the range of from about 2:1 up to about 6:1. The sulfuric acid used is concentrated sulfuric acid and is preferably from about 85 weight percent aqueous sulfuric acid up to about 95 weight percent aqueous sulfuric acid. The concentration of concentrated sulfuric acid used in the reaction mass may vary from about 15% up to about 40% based on the total weight of the reaction mass, with a concentration of sulfuric acid of about 20% being preferred.

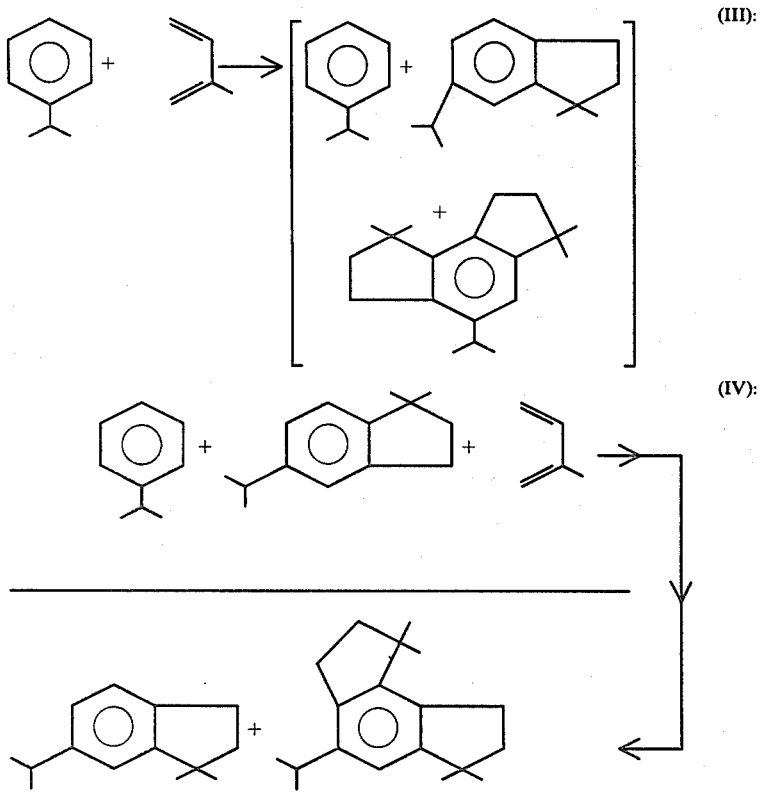

(III):

(IV):

The desired compound, 4-isopropyl-3,3,8,8-tetramethyl-as-hydrindacene is then preferably isolated as by fractional distillation.

Specific ranges of conditions for carrying out the reactions to form the precursor materials of our invention are also specifically set forth in U.S. Pat. No. 3,347,946 taken together with U.S. Pat. No. 3,078,319.

The resulting 4-isopropyl-3,3,8,8-tetramethyl-as-hydrindacene is then reacted with acetic anhydride in the presence of an aluminum chloride catalyst using one of three different addition modes:

1. The hydrindacene is charged to a mixture of aluminum chloride and acetic anhydride; or
2. The aluminum chloride is charged to a mixture of hydrindacene and acetic anhydride; or
3. The hydrindacene and acetic anhydride in admixture is added to aluminum chloride. Notwithstanding the specific addition mode used, the mole ratio of aluminum chloride to acetic anhydride may vary from about 2:1 up to about 4:1 with a preferred mole ratio of aluminum chloride:acetic anhydride of 3:1. The ratio of acetic anhydride:4-isopropyl-1,1,6,6-tetramethyl-as-hydrindacene may vary from about 0.8 up to 1.2. The solvent used in the reaction system is a chlorocarbon solvent such as carbon tetrachloride, o-dichlorobenzene, 1,1,2-trichloroethylene or tetrachloroethylene. The reaction temperature range may vary between about 0° C. and about 20° C.

When using the addition mode wherein the aluminum chloride is added to a stirred solution of hydrindacene, acetic anhydride and solvent, the reaction is carried out at about 0° C. yielding an approximately 60:40 mixture of the compounds having the structures:

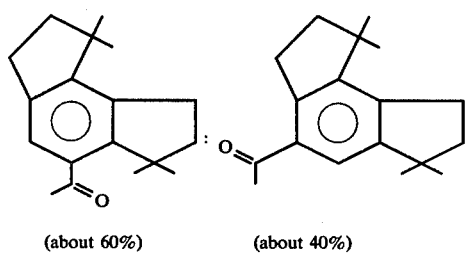

(about 60%)    (about 40%)

On the other hand, when a mixture of hydrindacene and acetic anhydride is added to a stirred slurry of aluminum chloride at a reaction temperature of about 0° C., a mixture of the four compounds having the following structures is obtained:

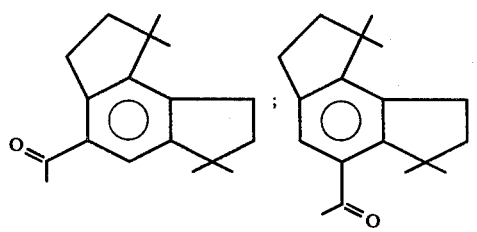

-continued

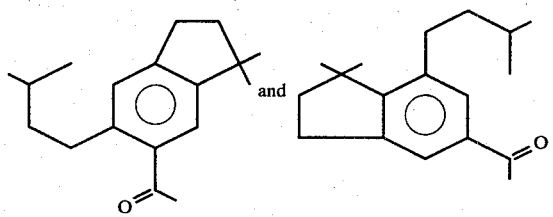

The compounds having the structures:

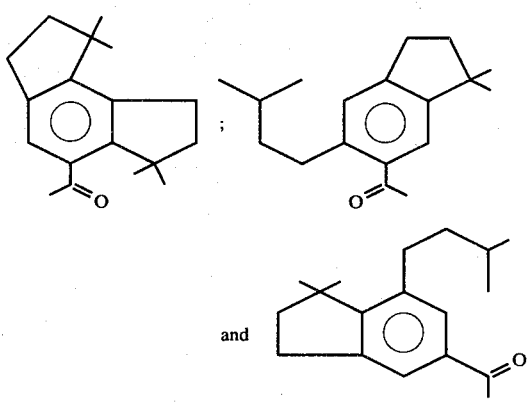

are novel compounds.

The acetyl hydrindacenes, acetyl indanes, mixtures of acetyl hydrindacenes and mixtures of acetyl hydrindacenes and acetyl indanes of our invention are capable of supplying and/or potentiating certain flavor and aroma notes usually lacking in many fruit flavors, wine flavors and tobacco flavors heretofore provided; particularly, peach flavors, apricot flavors and pear flavors. Furthermore, the acetyl hydrindacenes, acetyl indanes, mixtures of acetyl hydrindacenes and mixtures of acetyl hydrindacenes and acetyl indanes of our invention are capable of supplying certain fragrance notes usually lacking in many perfume materials, for example, musk fragrances.

When the acetyl hydrindacenes, acetyl indanes, mixtures of acetyl hydrindacenes and mixtures of acetyl hydrindacenes and acetyl indanes of our invention are used as food flavor adjuvants, the nature of the co-ingredients included with the said acetyl hydrindacenes, acetyl indanes, mixtures of acetyl hydrindacenes and mixtures of acetyl hydrindacenes and acetyl indanes in formulating the product composition will serve to alter the organoleptic characteristics of the ultimate foodstuff treated therewith.

As used herein in regard to flavors, the terms "alter" and "modify" in their various forms means "supplying or imparting flavor character or note to otherwise bland, relatively tasteless substances or augmenting the existing flavor characteristic where a natural flavor or synthetic flavor or mixture of natural and synthetic flavors is deficient in some regard, or supplementing the existing flavor impression to modify its quality, character or taste".

As used herein, the term "enhance" is intended to mean the intensification (without effecting a change in kind of quality or aroma or taste) of one or more taste and/or aroma nuances present in the organoleptic impression of a consumable material, e.g., foodstuff, tobacco, chewing gum, medicinal product, perfume composition or perfumed article.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "chewing gum" is intended to mean a composition which comprises a substantially water-insoluble, chewable plastic gum base such as chicle, or substitutes therefor, including jelutung, guttakay rubber and/or certain comestible natural or synthetic resins or waxes. Incorporated within the gum base, in admixture therewith may be plasticizers or softening agents, e.g., glycerine; and a flavoring composition which incorporates acetyl hydrindacenes, acetyl indanes, mixtures of acetyl hydrindacenes and mixtures of acetyl hydrindacenes and acetyl indanes of our invention, and, in addition, sweetening agents which may be sugars, including sucrose or dextrose and/or artificial sweeteners including dipeptides, cyclamates and saccharin. Other optional ingredients may also be present.

The term "medicinal product" includes both solids and liquids which are ingestible, non-toxic materials having medicinal value such as cough syrups, cough drops, toothpaste, aspirin and chewable medicinal tablets as further exemplified herein.

Substances suitable for use herein as co-ingredients or flavoring adjuvants are well known in the art for such use being extensively described in the relevant literature. Such material is required to be "ingestibly" acceptable and thus non-toxic or otherwise non-deleterious. Particularly critical is the additional requirement that such material be organoleptically compatible with acetyl hydrindacenes, acetyl indanes, mixtures of acetyl hydrindacenes and mixtures of acetyl hydrindacenes and acetyl indanes encompassed within the scope of our invention. Also critical is the additional requirement that such material be nonreactive (within the range of storage conditions and room temperature use conditions) with each of acetyl hydrindacenes, acetyl indanes, mixtures of acetyl hydrindacenes and mixtures of acetyl hydrindacenes and acetyl indanes.

Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxy toluene, (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agaragar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates, starches, pectins, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like; firming agents such as aluminum sodium sulfate, calcium chloride and calcium gluconate; texturizers, anti-caking agents, e.g., aluminum calcium sulfate and tribasic calcium phosphate; enzymes, yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethylacrolein, n-hexanal, 2-hexenel, cis-3-hexenal, 2-heptanal, 4-(p-hydroxyphenyl)-2-butanone, alpha-ionone, betaionone, methyl-3-butanone, 2-pentanone, 2-pentenal and propanol; alcohols such as 1-butanal, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-penten-2-ol, 1-penten-3-ol, p-hydroxyphenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylbutyrate, propyl acetate, amyl acetate, amyl butyrate, benzyl salicylate, dimethyl anthranilate, ethyl methylphenylglycidate, ethyl succinate, isobutyl cinnamate and terpenyl acetate; lactones, such as delta-decalactone, delta-undecalactone and delta-nonyl-lactone and gamma-undecalactone, gamma-dodecalatone and gamma nonyl-lactone as well as "peach" lactone; essential oils, such as jasmine absolute, rose absolute, orris absolute, lemon essential oil, Bulgarian rose, yara yara, natural raspberry oil and vanilla; lactones; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, be capable of providing an environment in which the acetyl hydrindacenes, acetyl indanes, mixtures of acetyl hydrindacenes and mixtures of acetyl hydrindacenes and acetyl indanes can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g, simulated foodstuffs, ingredients capable of providing normally solid compositions should be selected such as various cellulose derivatives.

As will be appreciated by those skilled in the art, the amount of acetyl hydrindacenes, acetyl indanes, mixtures of acetyl hydrindacenes and mixtures of acetyl hydrindacenes and acetyl indanes employed in a particular instance can vary over a relatively wide range whereby to its desired organoleptic effects having reference to the nature of the product are achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se or flavoring composition.

The use of insufficient quantities of acetyl hydrindacenes, acetyl indanes, mixtures of acetyl hydrindacenes and mixtures of acetyl hydrindacenes and acetyl indanes will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of acetyl hydrindacenes, acetyl indanes, mixtures of acetyl hydrindacenes and mixtures of acetyl hydrindacenes and acetyl indanes ranging from a small but effective amount, e.g., 0.001 parts per million up to about 50 parts per million by weight based on total composition are suitable. Concentrations in excess of the maximum quantity stated are not normally recommended, since they fail to prove commensurate enhancement of organoleptic properties. In those instances, wherein the acetyl hydrindacenes, acetyl indanes, mixtures of acetyl hydrindacenes and mixtures of acetyl hydrindacenes and acetyl indanes is added to the foodstuff as an integral component of a flavoring composition, it is, of course, essential that the total quantity of flavoring composition employed be sufficient to yield an effective concentration (of acetyl hydrindacenes, acetyl indanes, mixtures of acetyl hydrindacenes and mixtures of acetyl hydrindacenes and acetyl indanes) in the foodstuff product.

Food flavoring compositions prepared in accordance with the present invention preferably contain the acetyl hydrindacenes, acetyl indanes, mixtures of acetyl hydrindacenes and mixtures of acetyl hydrindacenes and acetyl indanes in concentrations ranging from about 0.1% up to about 15% by weight based on the total weight of the said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the acetyl hydrindacenes, acetyl indanes, mixtures of acetyl hydrindacenes and mixtures of acetyl hydrindacenes and acetyl indanes with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and acetyl hydrindacenes, acetyl indanes, mixtures of acetyl hydrindacenes and mixtures of acetyl hydrindacenes and acetyl indanes in a dry blender until the requisite degree of uniformity is achieved.

It is presently preferred to combine with acetyl hydrindacenes, acetyl indanes, mixtures of acetyl hydrindacenes and mixtures of acetyl hydrindacenes and acetyl indanes, the following adjuvants:

p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl pelargonate;
Methyl anthranilate;
Isoamyl acetate;
Isobutyl acetate;
Alpha ionone;
Ethyl butyrate;
Acetic acid;
Gamma-undecalactone;
Gamma-nonalactone
Gamma decalactone;
Delta undecalactone;
Delta dodecalactone;
Delta nonyl lactone;
"Peach" lactone;
Naphthyl ethyl ether;
Diacetyl;
Ethyl acetate;
Anethole;
Isoamyl butyrate;
Cis-3-hexenol-1;
2-Methyl-2-pentenoic acid;
Elemecine (4-allyl-1,2,6-trimethoxy benzene);
Isoelemecine (4-propenyl-1,2,6-trimethoxy benzene); and
2-(4-hydroxy-4-methylpentyl) norbornadiene prepared according to U.S. Application, Serial No. 539,093, now U.S. Pat. No. 3,911,029 issued on Oct. 7, 1975.

An additional aspect of our invention provides an organoleptically improved smoking tobacco product and additives therefor, as well as methods of making the same which overcome specific problems heretofore encountered in which specific desired woody flavor characteristics of natural tobacco are created or enhanced and may be readily controlled and maintained at the desired uniform level regardless of variations in the tobacco components of the blend.

The invention further provides improved tobacco additives and methods whereby various desirable sweet, floral and musk notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient acetyl hydrindacenes, acetyl indanes, mixtures of acetyl hydrindacenes and mixtures of acetyl hydrindacenes and acetyl indanes.

In addition to the acetyl hydrindacenes, acetyl indanes, mixtures of acetyl hydrindacenes and mixtures of acetyl hydrindacenes and acetyl indanes of our invention, other flavoring and aroma additives may be added to the smoking tobacco material or substitute therefor either separately or in mixture with the acetyl hydrindacenes, acetyl indanes, mixtures of acetyl hydrindacenes and mixtures of acetyl hydrindacenes and acetyl indanes as follows:

I. Synthetic Materials:

Beta-ethyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1,2-methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a-6,6,9a-tetramethyl naphtho(2,1-b)-furan;
4-Hydroxy hexanoic acid, gamma lactone;
Polyisoprenoid hydrocarbons defined in Example V of U.S. Pat. No. 3,589,372 issued on June 29, 1971.

II. Natural Oils:

Celery seed oil;
Coffee extract;
Bergamot Oil;
Cocoa extract;
Nutmeg oil;
Origanum oil An aroma and flavoring concentrate containing acetyl hydrindacenes, acetyl indanes, mixtures of acetyl hydrindacenes and mixtures of acetyl hydrindacenes and acetyl indanes and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of acetyl hydrindacenes, acetyl indanes, mixtures of acetyl hydrindacenes and mixtures of acetyl hydrindacenes and acetyl indanes to smoking tobacco material is between 125 ppm and 1,500 ppm (0.0125%–0.15%) of the active ingredients to the smoking tobacco material. We have further found that satisfactory results are obtained if the proportion by weight of the sum total of acetyl hydrindacenes, acetyl indanes, mixtures of acetyl hydrindacenes and mixtures of acetyl hydrindacenes and acetyl indanes used to flavoring material is between 1,000 and 10,000 ppm (0.10%–1.5%).

Any convenient method for incorporating the acetyl hydrindacenes, acetyl indanes, mixtures of acetyl hydrindacenes and mixtures of acetyl hydrindacenes and acetyl indanes in the tobacco product may be employed. Thus, the acetyl hydrindacenes, acetyl indanes, mixtures of acetyl hydrindacenes and mixtures of acetyl hydrindacenes and acetyl indanes taken alone or along with other flavoring additives may be dissolved in a suitable solvent such as ethanol, pentane, diethyl ether and/or other volatile organic solvents and the resulting solution may either be spread on the cured, cased and blended tobacco material or the tobacco material may be dipped into such solution. Under certain circumstances, a solution of acetyl hydrindacenes, acetyl indanes, mixtures of acetyl hydrindacenes, and mixtures of acetyl hydrindacenes and acetyl indanes taken alone or taken further together with other flavoring additives as set forth above may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the acetyl hydrindacenes, acetyl indanes, mixtures of acetyl hydrindacenes and mixtures of acetyl hydrindacenes and acetyl indanes in excess of the amounts or concentrations above indicated so that when blended with other tobaccos, the final product will have the percentage within the indicated range.

In accordance with one specific example of our invention, an aged, cured and shredded domestic burley tobacco is spread with a 10% ethyl alcohol solution of 6:4 mixture of compounds having the structures:

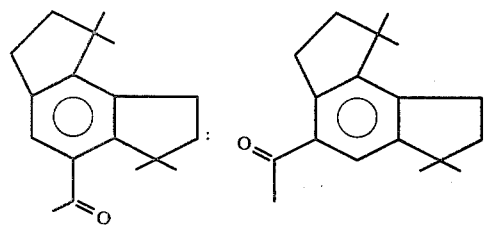

in an amount to provide a tobacco composition containing 400 ppm by weight of acetyl hydrindacene mixture on a dry basis. Thereafter, the alcohol is removed by evaporation and the tobacco is manufactured into cigarettes by the usual techniques. The cigarette when treated as indicated has a desired and pleasing aroma which is detectable in the main and side streams when the cigarette is smoked. This aroma is described as being sweeter, more aromatic, more tobacco-like and having excellent sweet, floral and musk-like notes.

While our invention is particularly useful in the manufacture of smoking tobacco, such as cigarette tobacco, cigar tobacco and pipe tobacco, other tobacco products formed from sheeted tobacco dust or fines may also be used. Likewise, the acetyl hydrindacenes, acetyl indanes, mixtures of acetyl hydrindacenes and mixtures of acetyl hydrindacenes and acetyl indanes of our invention can be incorporated with materials such as filter tip materials, seam paste, packaging materials, and the like which are used along with tobacco to form a product adapted for smoking. Furthermore, the acetyl hydrindacenes, acetyl indanes, mixtures of acetyl hydrindacenes and mixtures of acetyl hydrindacenes and acetyl indanes can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The acetyl hydrindacenes, acetyl indanes, mixtures of acetyl hydrindacenes and mixtures of acetyl hydrindacenes and acetyl indanes and one or more auxiliary perfume ingredients, including, for example, alcohols, aldehydes, nitriles, esters, cyclic esters, and natural essential oils, may be admixed so that the combined odors of the individual components produce a pleasant and desired fragrance particularly and preferably in musk and "animal-like" fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, the individual components which contribute its particular olfactory characteristics, but the over-all effect of the perfume composition will be the sum of the effects of each of the ingredients. Thus, the acetyl hydrindacenes, acetyl indanes, mixtures of acetyl hydrindacenes and mixtures of acetyl hydrindacenes and acetyl indanes can be used to alter the aroma characteristics of a perfume composition, for example, by utilizing or moderating the olfactory reaction contributed by another ingredient in the composition.

The amount of acetyl hydrindacenes, acetyl indanes, mixtures of acetyl hydrindacenes and mixtures of acetyl hydrindacenes and acetyl indanes of our invention which will be effective in perfume compositions depends on many factors, including the other ingredients, their amounts and the effects which are desired. It has been found that perfume compositions containing as little as 0.01% of acetyl hydrindacenes, acetyl indanes, mixtures of acetyl hydrindacenes and mixtures of acetyl hydrindacenes and acetyl indanes and even less (e.g., 0.005% can be used to impart a rich, animal-musk, sweet, sandalwood-like and floral notes to soaps, cosmetics or other products. The amount employed can range up to 10% of the fragrance components and will depend on considerations of cost, nature of the end product, the effect desired on the finished product and the particular fragrance sought.

The acetyl hydrindacenes, acetyl indanes, mixtures of acetyl hydrindacenes and mixtures of acetyl hydrindacenes and acetyl indanes are useful, taken alone or in perfume compositions as olfactory components in detergents, soaps, fabric softener compositions, fabric softener compositions for use in clothes dryers, space odorants and deodorants, perfumes, colognes, toilet water, bath preparations, such as bath oils, and bath solids; hair preparations, such as lacquers, brilliantines, creams, deodorants, hand lotions and sun screens; powders, such as talcs, dusting powders, face powders and the like. When used as an olfactory component as little as 1% of the acetyl hydrindacenes, acetyl indanes, mixtures of acetyl hydrindacenes and mixtures of acetyl hydrindacenes and acetyl indanes of our invention will suffice to impart an intense musk fragrance with sandalwood and floral notes to musk oil formulations. Generally, no more than 3% of the acetyl hydrindacenes, acetyl indanes, mixtures of acetyl hydrindacenes and mixtures of acetyl hydrindacenes and acetyl indanes based on the ultimate end product is required in the perfume composition.

In addition, the perfume composition or fragrance composition of our invention can contain a vehicle or carrier for the acetyl hydrindacenes, acetyl indanes, mixtures of acetyl hydrindacenes and mixtures of acetyl hydrindacenes and acetyl indanes. The vehicle can be a liquid such as an alcohol, a non-toxic alcohol, a non-toxic glycol, or the like. The carrier can also be an absorbent solid, such as a gum (e.g., gum arabic) or components for encapsulating the composition (such as gelatin).

It will thus be apparent that the acetyl hydrindacenes, acetyl indanes, mixtures of acetyl hydrindacenes and mixtures of acetyl hydrindacenes and acetyl indanes of our invention can be utilized to alter the sensory properties, particularly organoleptic properties, such as flavor and/or fragrance of a wide variety of consumable materials.

The following examples are illustrative and the invention is to be considered restricted thereto only as indicated in the appended claims. All parts and percentages given herein are by weight unless otherwise specified.

EXAMPLE I

PREPARATION OF
1,1-DIMETHYL-6-ISOPROPYLINDANE AND
4-ISOPROPYL-1,1,6,6-TETRAMETHYL-AS-HYDRINDACENE

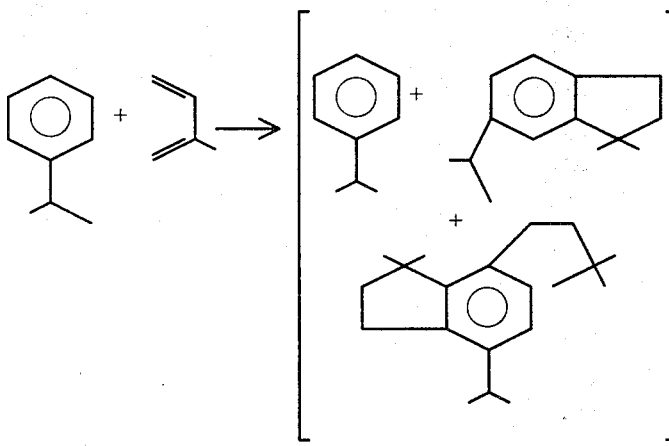

A solution of 510 grams of isoprene and 690 grams of cumene is added over a three-hour period to a well stirred mixture of 2910 grams of cumene and 903 grams of 90% sulfuric acid at 0°-5° C. The reaction mass is stirred for an additional 15 minutes and then stirring is stopped and the mixture is allowed to separate into two layers. The bottom layer is discarded. The top (organic) layer is washed with 600 ml of water, followed by washing with 2 liters of 5% sodium carbonate solution.

Distillation through a 1.5"×12" Goodloe packed column affords 2825 grams of cumene (b.p. 73° C., 50 mm Hg), 696 grams of 1,1-dimethyl-6-isopropylbenzene (b.p. 111° C., 11 mm Hg.) and 161 grams of 4-isopropyl-1,1,6,6-tetramethyl-as-hydrindacene (b.p. 134°–142° C., 3 mm Hg.).

Figure 1:
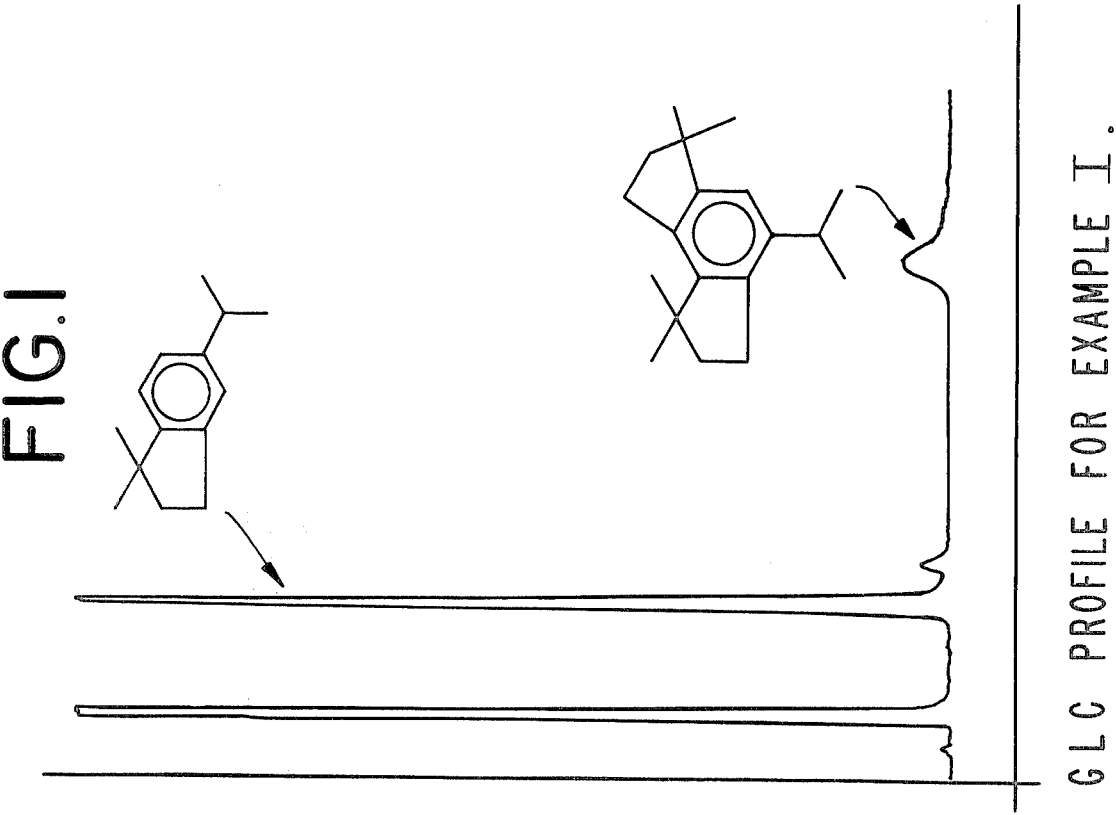
FIG. 1 is the GLC profile for the reaction product of Example I containing compounds having the structures.

The GLC of the reaction mass is shown in FIG. 1 (220° C. isothermal, 10% SE-30).

EXAMPLE II

PREPARATION OF
1,1-DIMETHYL-6-ISOPROPYLINDANE AND
4-ISOPROPYL-1,1,6,6-TETRAMETHYL-AS-HYDRINDACENE

Reaction:

-continued

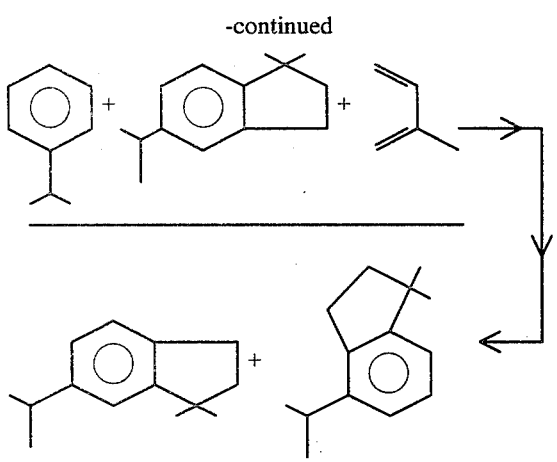

A solution of 158 grams of isoprene, 93 grams of cumene and 438 grams of 1,1-dimethyl-6-isopropylindane is added over a three-hour period to a well-stirred mixture containing 390 grams of 90% sulfuric acid, 187 grams of cumene and 878 grams of 1,1-dimethyl-6-isopropylbenzene at 0°–5° C. The reaction mass is stirred for an additional 15 minutes and then stirring is stopped and the mixture is allowed to separate into two layers. The bottom layer is discarded. The top (organic) layer is washed with 600 ml of water followed by washing with 2 liters of 5% sodium carbonate solution.

Distillation through a 1.5"×12" Goodloe packed column affords 199 grams of cumene, 1237 grams of 1,1-dimethyl-6-isopropylindane and 209 grams of 1,1,6,6-tetramethyl-as-hydrindacene.

The GLC of the reaction mass is shown in FIG. 2.

EXAMPLE III

PREPARATION OF 4-ACETYL-3,3,8,8-TETRAMETHYL-AS-HYDRINDACENE

Reaction:

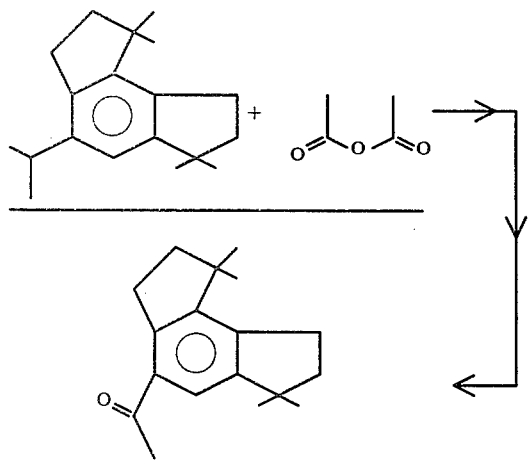

A solution of a mixture of 10 grams of 4-isopropyl-1,1,6,6-tetramethyl-as-hydrindacene and 8 grams of acetic anhydride in 20 ml of 1,1,1-trichloroethylene is added to a stirred slurry of of 18 grams of aluminum chloride in 25 ml of trichloroethylene at 20° C. over a ten minute period. The resulting mass is stirred for an additional ten minutes and then poured into 200 ml of ice water. The organic layer is washed and distilled to afford 8.2 grams of 4-acetyl-3,3,8,8-tetramethyl-as-hydrindacene.

The GLC trace in FIG. 3 shows the crude reaction mass (220° C. isothermal, 10% SE-30).

The NMR spectrum is shown in FIG. 4.

The IR spectrum is shown in FIG. 5.

EXAMPLE IV

PREPARATION OF A MIXTURE OF 4-ACETYL-1,1,6,6-TETRAMETHYL-AS-HYDRINDACENE AND 4-ACETYL-3,3,8,8-TETRAMETHYL-AS-HYDRINDACENE

Reaction:

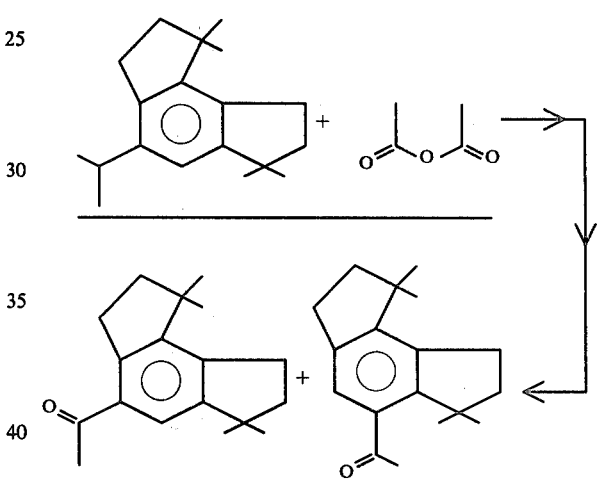

480 grams of aluminum chloride is added portionwise at 0° C. to a stirred solution of 256 grams of 4-isopropyl-1,1,6,6-tetramethyl-as-hydrindacene, 120 grams of acetic anhydride and 650 grams of trichloroethylene over a two-hour period. The reaction mass is stirred for an additional 15 minutes and quenched into 2 liters of ice water. The organic layer is washed twice, neutralizing with 5% sodium carbonate. Distillation through a short column afforded 199 grams of a mixture of 4-acetyl-1,1,6,6-tetramethyl-as-hydrindacene and 4-acetyl-3,3,8,8-tetramethyl-as-hydrindacene. The mixture is further purified using steam vacuum fractional distillation to afford a mobile liquid (b.p. 156° C., 3.0 mm Hg.).

The GLC spectrum of the crude reaction mass is shown in FIG. 6.

The NMR spectrum of the product is shown in FIG. 7.

The IR spectrum of the product is shown in FIG. 8.

EXAMPLE V

PREPARATION OF A MIXTURE OF

4-ACETYL-1,1,6,6-TETRAMETHYL-AS-HYDRINDACENE;

4-ACETYL-3,3,8,8-TETRAMETHYL-AS-HYDRINDACENE;

5-ACETYL-6-(3-METHYLBUTYL)-3,3-DIMETHYLINDANE; AND

5-ACETYL-7-(3-METHYLBUTYL)-1,1-DIMETHYLINDANE

Reaction:

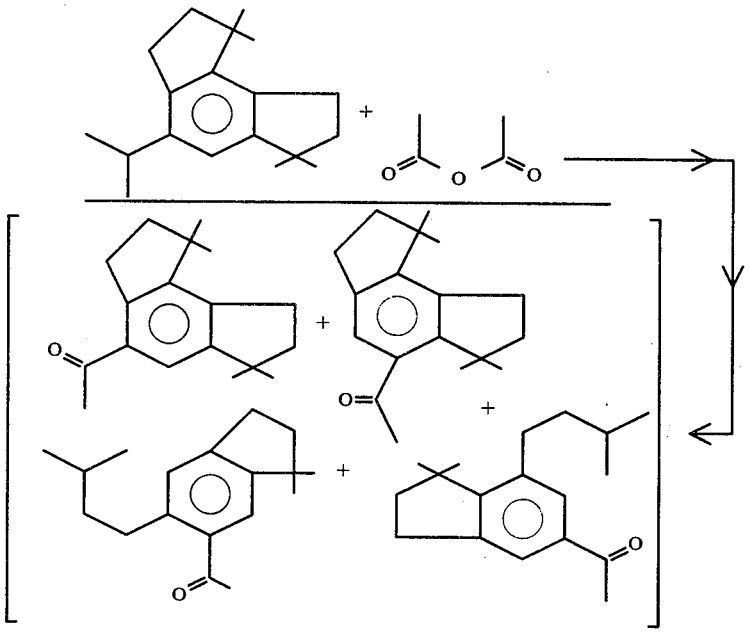

A solution of 168 grams of acetic anhydride, 384 grams of 4-acetyl-1,1,6,6-tetramethyl-as-hydrindacene and 700 grams of trichloroethylene is added at 0° C. to a stirred slurry of 661 grams of aluminum chloride in 700 grams of trichloroethylene over a two-hour period. After the addition, the reaction mass is warmed to room temperature and poured into 4 liters of ice water. The organic solution is washed with water and then washed with sodium bicarbonate solution. Distillation affords 323 grams of a mixture consisting of 4-acetyl-1,1,6,6-tetramethyl-as-hydrindacene, 4-acetyl-3,3,8,8-tetra-methyl-as-hydrindacene, 5-acetyl-6-(3-methylbutyl)-3,3-dimethylindane and 5-acetyl-7-(3-methylbutyl)-1,1-dimethylindane. The mixture is further purified by steam vacuum fractional distillation to afford a mobile liquid (b.p. 128°-132° C., 2.0 mm Hg.).

The GLC profile of the distilled product is shown in FIG. 9 (220° C. isothermal, 10% SE-30).

The NMR spectrum of 5-acetyl-6-(3-methylbutyl)-3,3-dimethylindane is shown in FIG. 10.

The IR spectrum of 5-acetyl-6-(3-methylbutyl)-3,3-dimethylindane is shown in FIG. 11.

The NMR spectrum of 5-acetyl-7-(3-methylbutyl)-1,1-dimethylindane is shown in FIG. 12.

The IR spectrum of 5-acetyl-7-(3-methylbutyl)-1,1-dimethylindane is shown in FIG. 13.

EXAMPLE VI

TOBACCO FORMULATION

A tobacco mixture is produced by admixing the following ingredients:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco. The following flavor formulation is prepared:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.1% to all of the cigarettes produced using the above tobacco formulation. Half of the cigarettes are then treated with 250 or 500 ppm of a mixture of acetyl indanes and acetyl hydrindacenes produced according to Example V. The control cigarettes not containing this composition of matter containing the mixture of acetyl hydrindacenes and acetyl indanes and the experimental cigarettes which contain the mixture of acetyl hydindacenes and acetyl indanes are evaluated by paired comparison and the results are set forth as follows:

The experimental cigarettes are found to have more body and thereby, on smoking, sweeter, enhanced tobacco-like, more aromatic with intense sweet, floral and musk notes.

All cigarettes are evaluated for smoke flavor with a 20 mm cellulose acetate filter.

It thus may be concluded that the mixture of acetyl hydrindacenes and acetyl indanes of Example V enhances the natural tobacco-like taste and aroma of a blended cigarette imparting to it, the sweet, floral and musk notes on smoking.

EXAMPLE VII

Granular detergent compositions prepared according to United Kingdom Pat. No. 1,501,498 having the following formulae are prepared by spray-drying the following mixtures as indicated in the columns headed VII A, VII B, VII C and VII D.

| Ingredient | Composition in % by Weight | | | |
|---|---|---|---|---|
| | Example VIIA | Example VIIB | Example VIIC | Example VIID |
| Sodium salt of ethoxylated fatty alcohol sulfate having an average of about 2.25 moles of ethylene oxide per mole of fatty alcohol (1) | 14.1 | 14.1 | 14.1 | 14.1 |
| Sodium tallow alkyl sulfate | 2.4 | 2.4 | 2.4 | 2.4 |
| Sodium silicate solids ratio: $SiO_2/Na_2O = 2.0$ | 0.0 | 2.0 | 6.0 | 0.0 |
| Sodium silicate solids ratio: $SiO_2/Na_2O = 3.2$ | 1.0 | 0.0 | 0.0 | 6.0 |
| Sodium tripolyphosphate | 24.0 | 24.0 | 24.0 | 24.0 |
| $Na_{12}(AlO_2 \cdot SiO_2)_{12} \cdot 27H_2O^{(2)}$ | 18.0 | 18.0 | 18.0 | 18.0 |
| Moisture | 10.0 | 10.1 | 9.9 | 10.2 |
| Sodium sulfate | 25.0 | 25.0 | 20.0 | 20.0 |
| Minor ingredients including sodium toluene sulfonate, trisodium sulfosuccinate, dyes, brighteners | 4.0 | 2.4 | 3.6 | 2.3 |
| Mixture of acetyl hydrindacenes and acetyl indanes prepared according to Example V | 1.5 | 0.0 | 0.0 | 0.0 |
| 6-acetyl-(3-methylbutyl)-1,1-dimethylindane prepared according to Example V | 0.0 | 2.0 | 0.0 | 0.0 |
| 4-acetyl-3,3,8,8-tetramethyl-as-hydrindacene prepared according to Example III | 0.0 | 0.0 | 2.0 | 0.0 |
| Mixture of acetyl hydrindacenes prepared according to Example IV | 0.0 | 0.0 | 0.0 | 3.0 |

[1] Fatty alcohol composition: 66% $C_{14}$; 33% $C_{16}$; 1% $C_{18}$.
[2] Prepared as described in United Kingdom Patent 1,501,498; average particle size diameter 2 microns.

Laundry solutions containing the above detergent compositions are used to launder fabrics. Each of the laundry compositions both prior to and on laundering gives rise to an intense musk aroma.

The composition of Example VII A has an intense animal-musky, sandalwood-like, and floral aroma. The composition of Example VII B has a sweet, musky, sandalwood-like, floral aroma. The composition of Example VII C has a rich, animal-musk character. The composition of Example VII D has a sweet, musk aroma with woody (sandalwood) nuances.

EXAMPLE VIII

PERFUMED LIQUID DETERGENT

Concentrated liquid detergents with animal-musky aromas are prepared containing 0.10%, 0.15% and 0.20% of a mixture of acetyl hydrindacenes having the structures:

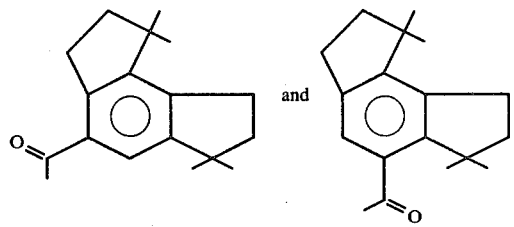

in a ratio of 4:6. They are prepared by adding and homogeneously mixing the appropriate quantity of mixture of acetyl hydrindacenes in liquid detergent. The liquid detergent is a builder-free liquid detergent consisting of (a) 50% of a non-ionic surfactant having an HLB of 8.0 and a critical micelle concentration of 0.007, weight percent at 25° C.; (b) an ionic surfactant which is triethanolamine citrate; and (c) one weight percent of diethanolamine prepared according to United Kingdom Pat. No. 1,491,603.

The detergents all possess animal-musky fragrances, the intensity increasing with greater concentrations of the mixture of actyl hydrindacenes.

When the acetyl hydrindacene mixture of Example IV is replaced with the 6-acetyl-5-(3-methylbutyl)-1,1-dimethylindane prepared according to Example V, the detergents all possess sweet, musk aromas with sandalwood undertones.

When the acetyl hydrindacene mixture of Example IV is replaced with the 4-acetyl-3,3,8,8-tetramethylas-hydrindacene prepared according to Example III, the resulting detergents all have sweet, musky aromas with sandalwood and floral undertones.

EXAMPLE IX

PEAR FLAVOR

The following pear flavor formulation is prepared:

| Ingredients | Parts by Weight |
|---|---|
| Methyl acetate | 0.20 |
| Ethyl acetate | 0.20 |
| Propyl acetate | 0.20 |
| Butyl acetate | 0.40 |
| Hexanol-1 | 0.30 |
| Amyl acetate | 2.55 |
| n-Hexyl acetate | 2.55 |
| Cis-3-hexenyl acetate | 8.44 |
| n-Heptyl acetate | 4.50 |
| Methyl-n-octanoate | 4.40 |
| Methyl-4-keto-trans-butene-2-oate | 6.20 |
| n-Heptanol | 4.01 |
| Methyl- | 9.20 |
| Methyl-trans-2-octenoate | 3.0 |
| n-Octanol | 4.2 |
| Ethyl-trans-2-octenoate | 2.5 |
| Methyl-cis-4-decenoate | 4.5 |

| Ingredients | Parts by Weight |
| --- | --- |
| Ethyl decanoate | 2.5 |
| Ethyl-trans-2-decenoate | 6.4 |
| Ethyl-3-hydroxy-octenoate | 6.4 |
| Ethyl-trans-2-trans-4-decadienoate | |
| Propyl-trans-2-trans-4-decadienoate | 7.4 |
| Butyl-trans-2-cis-4-decadienoate | 6.0 |
| Methyl-cis-8-tetradecenoate | 2.2 |
| Ethyl tetradecen-2-oate | 4.0 |
| Ethyl-cis-8-tetradecenoate | 8.0 |
| Mixture of acetyl hydrindacenes produced according to Example IV | 1.4 |

The mixture of acetyl hydrindacenes produced according to Example IV imparts a more natural pear-like aroma to this bartlett pear formulation. Replacement of the acetyl hydrindacene mixture of Example IV with the acetyl hydrindacene/acetyl indane mixture produced according to Example V enables one to use 50% less of the hydrindacene composition in order to produce the same "natural pear-like" effect.

EXAMPLE X

PEACH FLAVOR

The following peach flavor is prepared:

| Ingredients | Parts by Weight |
| --- | --- |
| Vanillin | 168.00 |
| Food grade aqueous 95% ethanol | 304.50 |
| Cinnamic aldehyde | 0.75 |
| Geraniol | 0.75 |
| Benzaldehyde | 4.00 |
| Amyl butyrate | 16.00 |
| Amyl acetate | 16.00 |
| Amyl valerate | 30.00 |
| Amyl formate | 36.00 |
| Capronic ether | 38.00 |
| Neroli oil | 48.00 |
| Ethyl valerianate | 88.00 |
| Aldehyde $C_{14}$ | 250.00 |
| 6-acetyl-5-(3-methylbutyl)-1,1-dimethylindane produced according to Example V | 7.00 |

The 6-acetyl-5-(3-methylbutyl)-1,1-dimethylindane produced according to Example V imparts a sweet, musky aroma and flavor characteristic to this peach formulation thereby rendering it much more natural-like and more aesthetically pleasing.

EXAMPLE XI

APRICOT FLAVOR FORMULATION

The following flavor formulation is prepared:

| Ingredients | Parts by Weight |
| --- | --- |
| Alpha ionone | 30.0 |
| Ethyl oenanthate | 30.0 |
| Benzaldehyde | 120.0 |
| Vanillin | 84.0 |
| Ethyl alcohol | 150.0 |
| Cinnamic aldehyde | 0.40 |
| Geraniol | 0.40 |
| Benzaldehyde | 2.00 |
| Amyl butyrate | 8.00 |
| Amyl acetate | 8.00 |
| Amyl valerate | 15.00 |
| Amyl formate | 18.00 |
| Capronic ether | 19.00 |
| Neroli oil | 20.00 |
| Ethyl valerianate | 44.0 |
| Aldehyde $C_{14}$ | 100.0 |
| Propylene glycol | 300.0 |
| Mixture of acetyl hydrindacenes produced according to Example IV | 8.0 |

The mixture of acetyl hydrindacenes produced according to Example IV adds a natural apricot nuance to this apricot flavor by adding sweet, musky aroma notes thereto.

EXAMPLE XII

A. POWDER FLAVOR

20 Grams of the flavor composition of Example IX which flavor composition contains a mixture of acetyl hydrindacenes is emulsified in a solution containing 300 grams gum acacia and 700 grams water. The emulsion is spray-dried with a Bowen Lab Model Drier utilizing 250 c.f.m. of air with an inlet temperature of 500° F., and outlet temperature of 200° F. and a wheel speed of 50,000 r.p.m.

B. PASTE BLEND

The following mixture is then prepared:

| Ingredients | Parts by Weight |
| --- | --- |
| Liquid Flavor Composition of Example IX | 48.4 |
| Cab-O-Sil M-5 (Brand of Silica produced by the Cabot Corporation of 125 High Street, Boston, Mass., 02110); Physical Properties: Surface Area: 200m$^2$/gm Nominal Particle Size: 0.012 microns Density: 2/3 lbs./cu.ft. | 3.2 |

The Cab-O-Sil is dispersed in any of the exemplified liquid flavor compositions with vigorous stirring, thereby resulting in a viscous liquid. 48.4 Parts by weight of the powder flavor composition prepared in Part A is then blended into the said viscous liquid, with stirring at 25° C. for a period of 30 minutes, resulting in a thixotropic sustained release flavor paste.

EXAMPLE XIII

CHEWING GUM

100 Parts by weight of chicle are mixed with 4 parts by weight of the flavor prepared in accordance with Example XII. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing the chewing gum has a pleasant long-lasting pear flavor.

EXAMPLE XIV

TOOTHPASTE FORMULATION

The following separate groups of ingredients are prepared:

| Group "A" | |
|---|---|
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium n-Lauroyl Sarcosinate (foaming agent) |
| Group "D" | |
| 1.200 | Flavor Material of Example XII |
| 100.00 (Total) | |

PROCEDURE:

1. To ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant pear flavor of constant strong intensity throughout said procedure (1–1.5 minutes).

EXAMPLE XV

CHEWABLE VITAMIN TABLETS

The flavor material produced according to the process of Example XII is added to a Chewable Vitamin Tablet Formulation at a rate of 5 gm/gm which Chewable Vitamin Tablet Formulation is prepared as follows:

| Ingredients | Gms/1000 Tablets |
|---|---|
| Vitamin C (ascorbic acid) as ascorbic acid-solution mixture 1:1 | 70.0 |
| Vitamin B$_1$ (thiamine mononitrate) as Rocoat ® thiamine mononitrate 33% (Hoffman La Roche) | 4.0 |
| Vitamin B$_2$ (riboflavin) as Rocoat ® riboflavin 33⅓% | 5.0 |
| Vitamin B$_6$ (pyridoxine hydrochloride) as Rocoat ® pyridoxide hydrochloride 33⅓% | 4.0 |
| Niacinamide as Rocoat ® niacinamide 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Certified lake color | 5.0 |
| Flavor of Example XII | 5.0 |
| Sweetener-sodium saccharin | 1.0 |
| Magnesium stearate lubricant | 10.0 |
| Mannitol q.s. to make | 500.0 |

Preliminary tablets are prepared by slugging, with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablet yields a pleasant, long-lasting, consistently strong pear flavor for a period of 12 minutes.

EXAMPLE XVI

MUSK PERFUME FORMULATION

The following musk perfume formulation is prepared:

| Ingredients | Parts by Weight |
|---|---|
| Musk Ambrette | 200 |
| Musk Ketone | 200 |
| Beta Ionone | 50 |
| Vetiveryl Acetate | 50 |
| Sandalwood Oil | 100 |
| Benzyl Benzoate | 400 |
| Mixture of acetyl indanes and acetyl hydrindacenes prepared according to Example V | 20 |

The mixture of the acetyl indanes and acetyl hydrindacenes of Example V imparts to this musk formulation, a natural "animal-musk", floral, woody, sandalwood-like undertone and causes it to be more "natural-like".

EXAMPLE XVII

PREPARATION OF A SOAP COMPOSITION

100 Grams of soap chips are mixed with 1 gram of the perfume composition of Example XVI until a substantially homogeneous composition is obtained. The perfumed soap composition manifests an excellent animal-musk, sandalwood, floral aroma.

EXAMPLE XVIII

PREPARATION OF A SOAP COMPOSITION

100 Grams of soap chips are mixed with 1 gram of the acetyl hydrindacene prepared according to Example III until a substantially homogeneous composition is obtained. The perfumed soap composition manifests an excellent musk aroma with woody and floral topnotes.

EXAMPLE XIX

PREPARATION OF A COLOGNE AND HANDKERCHIEF PERFUME

The mixture of acetyl hydrindacenes prepared according to Example IV is incorporated into a cologne at concentrations of 1.5%, 2.0%, 2.5%, 3.0%, 3.5% and 4.0% in 85% aqueous ethanol; and into handkerchief perfumes at concentrations of 15%, 20%, 25% and 30% (in 95% aqueous ethanol). Distinct and definite animal-musk fragrances are produced and imparted to the cologne and to the handkerchief perfume at each of the levels indicated.

EXAMPLE XX

PREPARATION OF A COSMETIC POWDER COMPOSITION

A cosmetic powder is prepared by mixing in a ball mill, 100 grams of talcum powder with 0.15 grams of the acetyl indane/acetyl hydrindacene mixture prepared according to Example V. The resulting powder has an excellent musk aroma with sandalwood and floral topnotes.

EXAMPLE XXI

SANDAL COLOGNE FORMULATION

The following "Sandal Cologne" perfume formulation is prepared:

| Ingredients | Parts by weight |
|---|---|
| Trimethyl-(2,2,3-norbornyl-5) 3-cyclohexanol-1 | 100 |
| 1',2',3',4',5',6',7',8',-octahydro 2',3',8',8',-tetramethyl-2'-acetonaphthone isomer mixture produced according to the process of Example VII of Application for U.S. Letters Pat. No. 434,948 filed on January 21, 1974 | 50 |
| 2,5,5-trimethyl acetyl cycloheptane produced according to Example I of U.S. Pat. Application 349,180 filed on April 9, 1973 | 10 |
| Eugenol (10% sol. in diethyl phthalate) | 5 |
| Borneol (1% sol. in ethyl alcohol) | 2 |
| Cedrenal (A tricyclic sesquiterpinic aldehyde derived from cedrene, having the structure: | 15 |

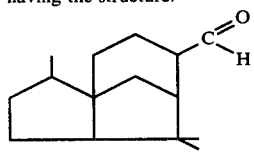

produced according to the process of U.S. Pat. Application 260,537 filed on June 7, 1972 (corresponding to published Dutch Appl. 7307849 laid open for public inspection on December 11, 1973)

| | |
|---|---|
| 2,2-Dimethyl-3-(2-(2,3-dimethyl-tricyclo-(2,2,1,0$^{2,6}$)-hept-3-yl) ethyl)-oxirane having the structure: | 50 |

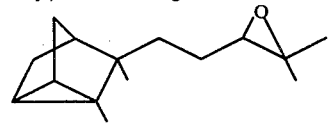

prepared according to Example II of U.S. Pat. 4,000,050 issued on December 28, 1976

| | |
|---|---|
| 4-acetyl-3,3,8,8-tetramethyl-as-hydrindacene having the structure: | 20 |

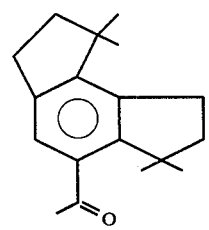

The use of the liquid 4-acetyl-3,3,8,8-tetramethyl-as-hydrindacene imparts a musky, sandalwood note to this East Indian sandalwood type formulation.

EXAMPLE XXII

SANDAL COLOGNE FORMULATION

The following sandal cologne perfume formulation is prepared:

| Ingredients | Parts by weight |
|---|---|
| Bergamot oil | 200 |
| Orange Flavor | 150 |
| Lemon Oil | 100 |
| Mandarin Oil | 50 |
| Eugenol | 10 |
| 4-(4-Methyl-4-hydroxy amyl) Δ$^3$-cyclohexene carboxaldehyde | 50 |
| 3-methyl-4(2,6,6-trimethyl-2-cyclohexen-1-yl)3-buten-2-one | 30 |
| Methyl-N-3,7-dimethyl-7-hydroxy-octylidene anthranilate | 5 |
| 6,7-dihydro-1,1,2,3,3-pentamethyl-4-(5H)-indanone having the structure: | 5 |

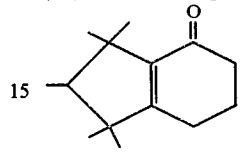

prepared according to Prep. A of Swiss Pat. 523,962

| | |
|---|---|
| 2-methyl-5-(2-endo-methyl-3-methylene-bicyclo-(2.2.1)hept-2-yl)-3-penten-2-ol | 100 |
| Mixture of acetyl hydrindacenes and acetyl indanes prepared according to Example V | 20 |

The mixture of acetyl hydrindacenes and acetyl indanes prepared according to Example V imparts to this formulation a sweet, musk aroma with woody (sandalwood-like) nuances in addition to the warm, woody, sandal aroma imparted to the formulation by the 2-methyl-5-(2-endo-methyl-3-methylene-bicyclo-[2.2.1]-hept-2-yl)-3-penten-2-ol prepared according to Example V of U.S. Pat. No. 4,000,050 issued on Dec. 28, 1976.

EXAMPLE XXIII

SANDAL COLOGNE FORMULATION

The following sandal cologne perfume formulation is prepared:

| Ingredients | Parts by Weight |
|---|---|
| Bergamot Oil | 200 |
| Orange Flavor | 150 |
| Lemon Oil | 100 |
| Mandarin Oil | 50 |
| Eugenol | 10 |
| 4-(4-Methyl-4-hyroxy amyl) Δ$^3$-cyclohexene carboxaldehyde | 50 |
| 3-methyl-4(2,6,6-trimethyl-2-cyclohexen-1-yl)3-buten-2-one | 30 |
| methyl-N-3,7-dimethyl-7-hydroxy-octylidene anthranilate | 5 |
| 6,7-dihydro-1,1,2,3,3-pentamethyl-4 5(H)indanone having the structure: | 5 |

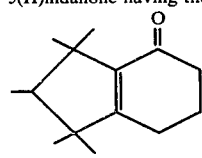

prepared according to Prep. A of Swiss Pat. 523,962

| | |
|---|---|
| 2-methyl-5(2-exo-methyl-3-methylene-bicyclo-[2.2.1]-hept-2-yl)3-penten-2-ol | 100 |
| 6-acetyl-5-(3-methylbutyl)-1,1-dimethyl-indane prepared according to Example V | 30 |

The 6-acetyl-5-(3-methylbutyl)-1,1-dimethylindane imparts to this sandal cologne formulation a sweet, musk aroma note with woody (sandalwood) undertones. This is in addition to the warm, woody, sandal aroma note imparted by the 2-methyl-5(2-exo-methyl-3-methylene-bicyclo-[2.2.1]-hept-2-yl)-3-penten-2-ol.

EXAMPLE XXIV

PREPARATION OF A COLOGNE AND HANDKERCHIEF PERFUME

The composition of Example XXIII is incorporated into colognes at concentrations of 2.0%, 2.5%, 3.0%, 3.5% and 4.0% in 85% aqueous food-grade ethanol and into handkerchief perfumes in concentrations of 15%, 20%, 25% and 30% (in 95% aqueous ethanol). The use of the perfume composition of Example XXIII affords a distinct and definite "sandal cologne" aroma having a warm, sandalwood-like character and definitive sweet, musk undertones to the handkerchief perfume and to the cologne.

EXAMPLE XXV

The following basic pear flavor formulation is prepared:

| Ingredients | Parts by Weight |
|---|---|
| Vanillin | 2.0 |
| Hexyl Acetate | 8.0 |
| Hexyl Isobutyrate | 20.0 |
| Trans-2-hexenal (10% in food grade ethanol) | 2.0 |
| Hexanal | 0.5 |
| Apple Fusel Oil | 10.0 |
| Linalyl Isobutyrate | 0.5 |
| Hexyl-2-methylbutyrate | 10.0 |
| Sage Sclaree (10% in food grade ethanol) | 0.5 |
| Coriander Oil | 0.5 |
| Food grade ethanol (95% aqueous) | 146.0 |
| Propylene Glycol | 800.0 |

The above flavor is divided into two portions. To a first portion 0.02% by weight of the mixture of acetyl hydrindacenes prepared according to Example IV is added to the basic pear flavor. To the other half of the formulation, nothing is added. Both flavors are compared at the rate of 50 ppm in water and evaluated by a bench panel of three experienced tasters. All the members of the panel state that the flavor with the mixture of acetyl hydrindacenes prepared according to Example IV has a more natural, riper pear character. The flavor containing the mixture of acetyl hydrindacenes is considered as fuller and has a longer lasting aftertaste. The flavor appears to be enhanced by the mixture of acetyl hydrindacenes prepared according to Example IV. Therefore, it is unanimously preferred.

EXAMPLE XXVI

Utilizing the procedure of Example I of column 15 of United States Patent 3,632,396, a nonwoven cloth substrate useful as a dryer-added fabric-softening article of manufacture is prepared wherein the substrate, the substrate coating and the outer coating and the perfuming material are as follows:
1. a water "dissolvable" paper ("Dissolvo Paper"):
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent
   1 percent of an acetyl hydrindacene, an acetyl indane, a mixture of acetyl hydrindacenes or a mixture of acetyl hydrindacenes and acetyl indanes as set forth in the Table I below and giving rise to the aroma nuances as set forth in said Table I below:

TABLE I

| Description Of Composition | Flavor Characteristics |
|---|---|
| Mixture of acetyl hydrindacenes and acetyl indanes prepared according to Example V | An intense animal-musky, sandalwood-like, and floral aroma |
| 6-acetyl-(3-methylbutyl)-1,1-dimethylindane prepared according to Example V | A sweet, musky, sandalwood-like, floral aroma. |
| 4-acetyl-3,3,8,8-tetramethyl-as-hydrindacene prepared according to Example III | A rich, animal-musk character |
| Mixture of acetyl hydrindacene prepared according to Example IV | A sweet, musk aroma with woody (sandalwood) nuances |

Fabric-softening compositions prepared as set forth above having the above aroma characteristics essentially consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aromas as set forth in Table I above are imparted in a pleasant manner to the head space in the dryer on operation thereof using the said dryer added fabric softening nonwoven fabric.

What is claimed is:
1. A process for augmenting or enhancing the pear, peach or apricot flavor of a foodstuff having a pear, peach or apricot flavor comprising the step of intimately admixing with said foodstuff from 0.001 ppm up to about 50 ppm by weight based on said foodstuff of a mixture of a 60:40 mixture of chemicals having, respectively, the structures:

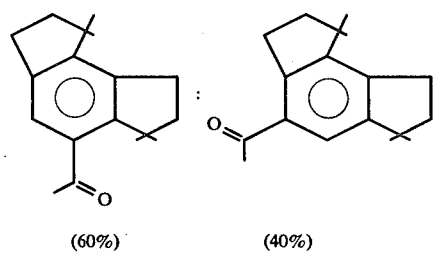

(60%)      (40%)

* * * * *